(12) United States Patent
Wagman et al.

(10) Patent No.: US 9,994,550 B2
(45) Date of Patent: Jun. 12, 2018

(54) HETEROCYCLIC MODULATORS OF LIPID SYNTHESIS FOR USE AGAINST CANCER AND VIRAL INFECTIONS

(71) Applicant: 3-V Biosciences, Inc., Menlo Park, CA (US)

(72) Inventors: Allan S. Wagman, Belmont, CA (US); Russell J. Johnson, Sunnyvale, CA (US); Cristiana A. Zaharia, Redwood City, CA (US); Haiying Cai, Cupertino, CA (US); Lily W. Hu, Palo Alto, CA (US); Greg Duke, Menlo Park, CA (US); Yamini Ohol-Gupta, Menlo Park, CA (US); Timothy Heuer, Menlo Park, CA (US); Marie O'Farrell, Menlo Park, CA (US)

(73) Assignee: 3-V Biosciences, Inc., Menlo Park, CA (US)

( * ) Notice: Subject to any disclaimer, the term of this patent is extended or adjusted under 35 U.S.C. 154(b) by 0 days. days.

(21) Appl. No.: 15/110,154

(22) PCT Filed: Jan. 7, 2015

(86) PCT No.: PCT/US2015/010459
§ 371 (c)(1),
(2) Date: Jul. 7, 2016

(87) PCT Pub. No.: WO2015/105860
PCT Pub. Date: Jul. 16, 2015

(65) Prior Publication Data
US 2016/0326141 A1    Nov. 10, 2016

Related U.S. Application Data

(60) Provisional application No. 61/924,520, filed on Jan. 7, 2014.

(51) Int. Cl.
| | | |
|---|---|---|
| *C07D 403/00* | (2006.01) | |
| *C07D 401/00* | (2006.01) | |
| *A61K 31/445* | (2006.01) | |
| *A61K 31/415* | (2006.01) | |
| *C07D 403/10* | (2006.01) | |
| *C07D 405/14* | (2006.01) | |
| *C07D 401/10* | (2006.01) | |
| *A61K 31/4155* | (2006.01) | |
| *A61K 31/454* | (2006.01) | |
| *A61K 45/06* | (2006.01) | |

(52) U.S. Cl.
CPC ........ *C07D 403/10* (2013.01); *A61K 31/4155* (2013.01); *A61K 31/454* (2013.01); *A61K 45/06* (2013.01); *C07D 401/10* (2013.01); *C07D 405/14* (2013.01)

(58) Field of Classification Search
CPC .............. A61K 31/454; A61K 31/4162; C07D 401/10; C07D 403/10
USPC ................ 548/364.1; 546/211; 514/326, 403
See application file for complete search history.

(56) References Cited

FOREIGN PATENT DOCUMENTS

| | | |
|---|---|---|
| WO | WO 2008/075064 A1 | 6/2008 |
| WO | WO 2008/075070 A1 | 6/2008 |
| WO | WO 2008/075077 A1 | 6/2008 |
| WO | WO 2012/122391 A1 | 9/2012 |
| WO | WO 2014/008197 A1 | 1/2014 |

OTHER PUBLICATIONS

Browne, C.D., et al., "Inhibition of endothelial cell proliferation and angiogenesis by orlistat, a fatty acid synthase inhibitor", (2006) *FASEB J.*, 20(12):2027-2035.
Chakravarthy, M.V., et al. ""New" hepatic fat activates PPARα to maintain glucose, lipid, and cholesterol homeostasis", (2005) *Cell Metab.* 1:309-322.
Flavin, R., et al., "Fatty acid synthase as a potential therapeutic target in cancer", (2010) *Future Oncol.*, 6(4):551-562.
Orita, R. et al., "Selective Inhibition of Fatty Acid Synthase for Lung Cancer Treatment", (2007) *Clin. Cancer Res.*, 13(23):7139-7145.
Puig, T. et al., "A novel inhibitor of fatty acid synthase shows activity against HER2+ breast cancer xenografts and is active in anti-HER2 drug-resistant cell lines", (2011) *Breast Cancer Res.*, 13(6):R131.
Wu, M. et al., "Antidiabetic and antisteatotic effects of the selective fatty acid synthase (FAS) inhibitor platensimycin in mouse models of diabetes", (2011) *PNAS* 108(13):5378-5383.

*Primary Examiner* — Shengjun Wang
(74) *Attorney, Agent, or Firm* — Cooley LLP

(57) ABSTRACT

Heterocyclic modulators of lipid synthesis are provided as well as pharmaceutically acceptable salts thereof; pharmaceutical compositions comprising such compounds; and methods of treating conditions characterized by dysregulation of a fatty acid synthase pathway by the administration of such compounds.

18 Claims, No Drawings

HETEROCYCLIC MODULATORS OF LIPID SYNTHESIS FOR USE AGAINST CANCER AND VIRAL INFECTIONS

CROSS-REFERENCE TO RELATED APPLICATIONS

This application is a U.S. National Phase application, filed under 35 U.S.C. § 371, of International Application No. PCT/US2015/010459, filed Jan. 7, 2015, which claims the benefit under 35 U.S.C. § 119(e) of U.S. provisional Patent Application No. 61/924,520, filed Jan. 7, 2014. The foregoing applications are incorporated herein by reference in their entireties.

FIELD

The present disclosure relates generally to heterocyclic modulators of lipid synthesis and methods of use thereof. The present heterocyclic modulators of lipid synthesis can be used for the treatment of disorders characterized by disregulation in the fatty acid synthase function in a subject by modulating the fatty acid synthase pathway and/or the fatty acid synthase function.

BACKGROUND

Viral disease is a significant health concern that threatens large segments of human populations. Some of the features related to viral infection which are of concern to health care professionals include its highly contagious nature (e.g., HIV, SARS, etc.) and high mutability. Some viruses are also oncogenic (such as HPV, EBV and HBV). While viruses are structurally amongst the simplest of organisms, they are regarded to be among the most difficult to control and present a formidable challenge for antiviral drug R&D.

Thus far, there have been a few antiviral drugs widely used in patients, such as Amantadine and Oseltamivir for influenza, Acyclovir for HSV-related infections, Ganciclovir for CMV infection, and multiple agents including co-formulated drugs (Efavirenz, emtricitabine, and tonfovir disoproxil fumarate) for AIDS treatments. These drugs possess a variety of undesirable neurological, metabolic and immunological side-effects. Therefore, development of new antiviral therapy has become a major focus of medical and pharmaceutical research and development.

Infection by hepatitis C virus (HCV) is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves combination therapy with interferon-alpha and ribavirin, often with the addition of a direct-acting protease inhibitor (Telaprevir or Boceprevir). The treatment is cumbersome and sometimes has debilitating and severe side effects. For this reason, many patients are not treated in early stages of the disease. Additionally, some patient populations do not durably respond to treatment. New and effective methods of treating HCV infection are urgently needed.

The dominant therapeutic approaches that are currently employed to treat cancer include surgical removal of primary tumors, tumor irradiation, and parenteral application of anti-mitotic cytotoxic agents. Unfortunately, only a relatively small cross-section of cancer patients have tumors that are "addicted" to a specific pathway, and can therefore be treated with newer targeted agents. The continued dominance of these long established therapies is mirrored by the lack of improvement in survival rates for most cancers. In addition to limited clinical success, devastating side effects accompany classic therapies. Both radiation- and cytotoxic-based therapies result in the destruction of rapidly dividing hematopoietic and intestinal epithelial cells leading to compromised immune function, anemia, and impaired nutrient absorption. Surgical intervention often results in a release of tumor cells into the circulation or lymph systems from which metastatic tumors can subsequently be established. Improved methods for the treatment of cancer are needed.

SUMMARY

The present disclosure addresses the deficiencies for antiviral and anticancer treatments by providing novel heterocyclic modulators of lipid synthesis having improved antiviral and anticancer activities.

In various aspects, the present disclosure provides for compounds of Structure I:

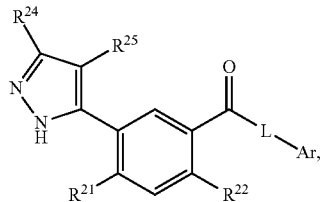

or a pharmaceutically acceptable salt thereof, wherein:
L-Ar is

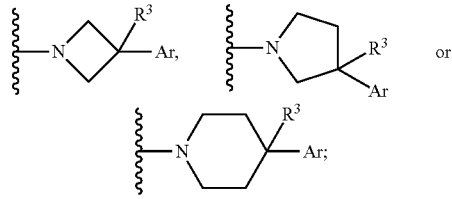

Ar is

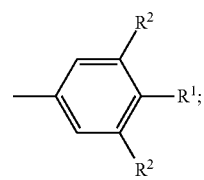

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen;

wherein the compound is not:

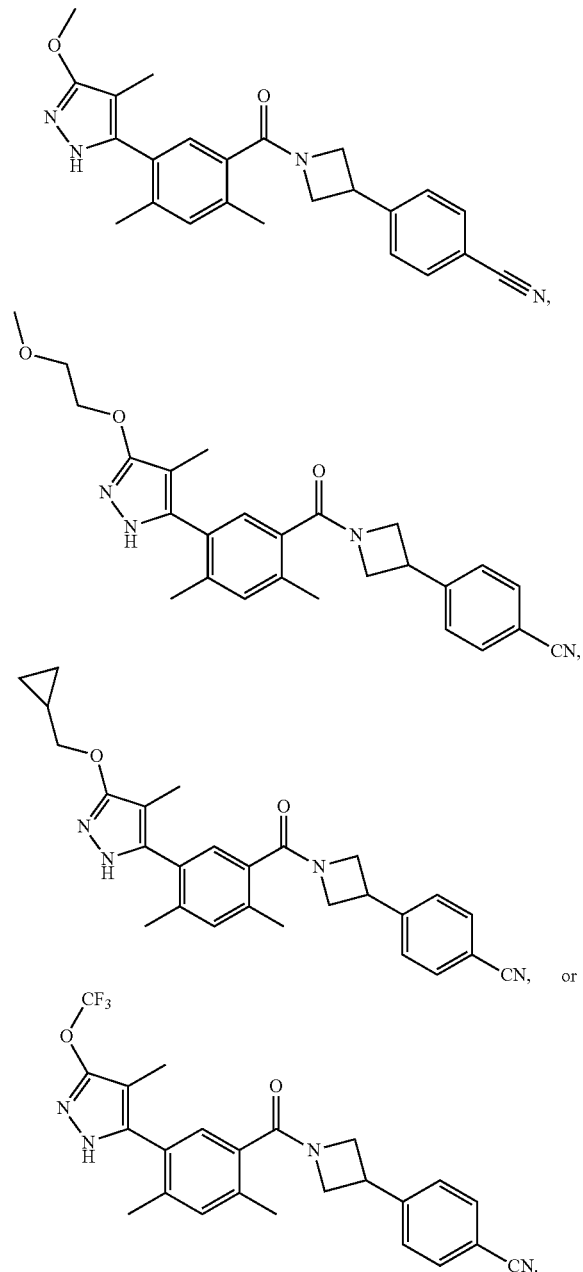

In various aspects, the present disclosure provides pharmaceutical compositions comprising any of the compounds of Structure I and a pharmaceutically acceptable carrier, excipient, or diluent.

In various aspects, the present disclosure provides methods of treating a condition characterized by disregulation of a fatty acid synthase pathway in a subject, the method comprising administering to a subject in need of such treatment a therapeutically effective amount of any of the compounds of Structure I.

In various aspects, the condition characterized by disregulation of a fatty acid synthase pathway is a viral infection or cancer. In various aspects, the viral infection is a hepatitis C infection. In various aspects, the cancer is breast cancer, lung cancer, ovarian cancer, pancreatic cancer or colon cancer.

In various aspects, wherein the condition characterized by disregulation of a fatty acid synthase pathway is a viral infection, the viral infection is treated using any of the compounds of Structure I in combination with one or more additional antiviral agents. In various aspects, wherein the condition characterized by disregulation of a fatty acid synthase pathway is cancer, the cancer is treated using any of the compounds of Structure I in combination with one or more additional cancer therapeutic agents.

DETAILED DESCRIPTION

The present disclosure addresses the deficiencies in treating conditions characterized by disregulation of the FASN function in a subject, such as viral infection, cancer and metabolic disorders, by providing novel heterocyclic modulators of lipid synthesis.

In certain aspects, the present disclosure provides compositions and methods for treatment of viral infections. In general, the compositions and methods for treatment of viral infections are directed toward modulation of the fatty acid synthesis pathway. The fatty acid synthesis pathway is involved in the replication of viruses in the host cells. The present disclosure embodies methods for the treatment of viral infections that interact with the fatty acid synthesis pathway, such as hepatitis C.

In certain aspects, the present disclosure provides compositions and methods for the treatment of cancer. Fatty acid synthase is responsible for conversion of malonyl-CoA into long-chain fatty acids, which is an early reaction in fatty acid biosynthesis. Fatty acid synthase is overexpressed in many cancer cells. Without being bound by any particular theory, it is hypothesized that inhibition of fatty acid synthase expression or fatty acid synthase activity selectivity suppresses proliferation and induces cell death of cancer cells, with little toxicity towards normal cells.

Further, the present disclosure provides compounds and methods for modulating host cell targets that are targeted by viruses. Such modulation of host cell targets can include either activation or inhibition of the host cell targets. Accordingly, compounds that modulate components of the fatty acid synthesis pathway, such as the activity of a non-viral protein, e.g., a host cell protein, can be used as antiviral pharmaceutical agents.

Definitions

Chemical moieties referred to as univalent chemical moieties (e.g., alkyl, aryl, etc.) also encompass structurally permissible multivalent moieties, as understood by those skilled in the art. For example, while an "alkyl" moiety generally refers to a monovalent radical (e.g., $CH_3CH_2$—), in appropriate circumstances an "alkyl" moiety can also refer to a divalent radical (e.g., —$CH_2CH_2$—, which is equivalent to an "alkylene" group). Similarly, under circumstances where a divalent moiety is required, those skilled in the art will understand that the term "aryl" refers to the corresponding divalent arylene group.

All atoms are understood to have their normal number of valences for bond formation (e.g., 4 for carbon, 3 for N, 2 for O, and 2, 4, or 6 for S, depending on the atom's oxidation state). On occasion a moiety can be defined, for example, as $(A)_aB$, wherein a is 0 or 1. In such instances, when a is 0 the moiety is B and when a is 1 the moiety is AB.

Where a substituent can vary in the number of atoms or groups of the same kind (e.g., alkyl groups can be $C_1, C_2, C_3$, etc.), the number of repeated atoms or groups can be represented by a range (e.g., $C_1$-$C_6$ alkyl) which includes each and every number in the range and any and all sub ranges. For example, $C_1$-$C_3$ alkyl includes $C_1, C_2, C_3, C_{1-2}, C_{1-3}$, and $C_{2-3}$ alkyl.

"Alkanoyl" refers to a carbonyl group with a lower alkyl group as a substituent.

"Alkylamino" refers to an amino group substituted by an alkyl group.

"Alkoxy" refers to an O-atom substituted by an alkyl group as defined herein, for example, methoxy [—$OCH_3$, a $C_1$alkoxy]. The term "$C_{1-6}$ alkoxy" encompasses $C_1$ alkoxy, $C_2$ alkoxy, $C_3$ alkoxy, $C_4$ alkoxy, $C_5$ alkoxy, $C_6$ alkoxy, and any sub-range thereof.

"Alkoxycarbonyl" refers to a carbonyl group with an alkoxy group as a substituent.

"Alkylcarbonyloxy" refers to the group —O—(C=O)-alkyl.

"Alkyl," "alkenyl," and "alkynyl," refer to optionally substituted, straight and branched chain aliphatic groups having from 1 to 30 carbon atoms, or preferably from 1 to 15 carbon atoms, or more preferably from 1 to 6 carbon atoms. Examples of alkyl groups include, without limitation, methyl, ethyl, propyl, isopropyl, butyl, tert-butyl, isobutyl, pentyl, hexyl, vinyl, allyl, isobutenyl, ethynyl, and propynyl. The term "heteroalkyl" as used herein contemplates an alkyl with one or more heteroatoms. The term "haloalkyl" as used herein contemplates an alkyl having one to three halogen substituents.

"Alkylene" refers to an optionally substituted divalent radical which is a branched or unbranched hydrocarbon fragment containing the specified number of carbon atoms, and having two points of attachment. An example is propylene [—$CH_2CH_2CH_2$—, a $C_3$alkylene].

"Amino" refers to the group —$NH_2$.

"Aryl" refers to optionally substituted aromatic groups which have at least one ring having a conjugated pi electron system and includes carbocyclic aryl, and biaryl groups, all of which can be optionally substituted. Phenyl and naphthyl groups are preferred carbocyclic aryl groups.

"Aralkyl" or "arylalkyl" refer to alkyl-substituted aryl groups. Examples of aralkyl groups include butylphenyl, propylphenyl, ethylphenyl, methylphenyl, 3,5-dimethylphenyl, tert-butylphenyl.

"Carbamoyl" s used herein contemplates a group of the structure

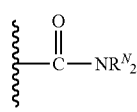

where in $R^N$ is selected from the group consisting of hydrogen, —OH, $C_1$ to $C_{12}$ alkyl, $C_1$ to $C_{12}$ heteroalkyl, alkenyl, alkynyl, cycloalkyl, heterocycle, aryl, heteroaryl, aralkyl, alkoxy, alkoxycarbonyl, alkanoyl, carbamoyl, sulfonyl, sulfonate and sulfonamide.

"Carbonyl" refers to a group of the structure

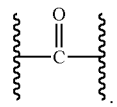

"Cycloalkyl" refers to an optionally substituted ring, which can be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Heterocycle" refers to an optionally substituted 5- to 7-membered cycloalkyl ring system containing 1, 2 or 3 heteroatoms, which can be the same or different, selected from N, O or S, and optionally containing one double bond. "Heterocycle" also refers to an optionally substituted 4- to 8-membered cycloalkyl ring system containing 1, 2 or 3 heteroatoms, which can be the same or different, selected from N, O or S, and optionally containing one double bond.

"Halogen" refers to a chloro, bromo, fluoro or iodo atom radical. The term "halogen" also contemplates terms "halo" or "halide."

"Heteroatom" refers to a non-carbon atom, where boron, nitrogen, oxygen, sulfur and phosphorus are preferred heteroatoms, with nitrogen, oxygen and sulfur being particularly preferred heteroatoms in the compounds of the present disclosure.

"Heteroaryl" refers to optionally substituted aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include thienyl, pyrryl, furyl, pyridyl, pyrimidyl, pyrazinyl, pyrazolyl, oxazolyl, isoxazolyl, imidazolyl, thiazolyl, pyranyl, tetrazolyl, pyrrolyl, pyrrolinyl, pyridazinyl, triazolyl, indolyl, isoindolyl, indolizinyl, benzimidazolyl, quinolyl, isoquinolyl, indazolyl, benzotriazolyl, tetrazolopyridazinyl, oxadiazolyl, benzoxazolyl, benzoxadiazolyl, thiadiazolyl, benzothiazolyl, benzothiadiazolyl, and the like.

An "optionally substituted" moiety can be substituted with from one to four, or preferably from one to three, or more preferably one or two non-hydrogen substituents. Unless otherwise specified, when the substituent is on a carbon, it is selected from the group consisting of —OH, —CN, —$NO_2$, halogen, $C_1$-$C_{12}$ alkyl, $C_1$-$C_{12}$ heteroalkyl, cycloalkyl, heterocycle, aryl, heteroaryl, aralkyl, alkoxy, alkoxycarbonyl, alkanoyl, carbamoyl, sulfonyl, sulfonate, sulfonamide and amino, none of which are further substituted. Unless otherwise specified, when the substituent is on a carbon, it may also be selected from the group consisting of oxo. Unless otherwise specified, when the substituent is on a carbon, it may also be selected from the group consisting of alkylcarbonyloxy, which is not further substituted. Unless otherwise specified, when the substituent is on a carbon, it may also be selected from the group consisting of alkylamino, which is not further substituted. Unless otherwise specified, when the substituent is on a carbon, it may also be selected from the group consisting of $C_1$-$C_{12}$alkenyl and $C_1$-$C_{12}$ alkynyl, neither of which are further substituted. Unless otherwise specified, when the substituent is on a nitrogen, it is selected from the group consisting of $C_1$-$C_{12}$ alkyl, $C_1$-$C_{12}$ heteroalkyl, cycloalkyl, heterocycle, aryl, heteroaryl, aralkyl, alkoxy, alkoxycarbonyl, alkanoyl, carbamoyl, sulfonyl, sulfonate and sulfonamide, none of which are further substituted. Unless otherwise specified, when the substituent is on a nitrogen, it may also be selected from the group consisting of $C_1$-$C_{12}$ alkenyl and $C_1$-$C_{12}$ alkynyl, neither of which are further substituted.

"Oxo" refers to the =O substituent.

The term "sulfonamide" as used herein contemplates a group having the structure

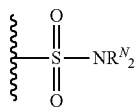

wherein $R^N$ is selected from the group consisting of hydrogen, —OH, $C_1$-$C_{12}$ alkyl, $C_1$-$C_{12}$ heteroalkyl, alkenyl, alkynyl, cycloalkyl, heterocycle, aryl, heteroaryl, aralkyl, alkoxy, alkoxycarbonyl, alkanoyl, carbamoyl, sulfonyl, sulfonate and sulfonamide.

The term "sulfonate" as used herein contemplates a group having the structure

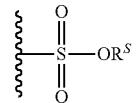

wherein $R^S$ is selected from the group consisting of hydrogen, $C_1$-$C_{10}$ alkyl, $C_2$-$C_{10}$ alkenyl, $C_2$-$C_{10}$ alkynyl, $C_1$-$C_{10}$ alkanoyl, or $C_1$-$C_{10}$ alkoxycarbonyl.

"Sulfonyl" as used herein alone or as part of another group, refers to an $SO_2$ group. The $SO_2$ moiety is optionally substituted. In particular, "sulfonyl" as used herein contemplates a group having the structure

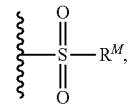

wherein $R^M$ is selected from the group consisting of hydrogen, $C_1$-$C_{12}$ alkyl, $C_1$-$C_{12}$ heteroalkyl, alkenyl, alkynyl, cycloalkyl, heterocycle, aryl, heteroaryl, aralkyl and alkoxy.

Compounds of the present disclosure can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present disclosure contemplates various stereoisomers and mixtures thereof and are specifically included within the scope of the present disclosure. Stereoisomers include enantiomers, diastereomers, and mixtures of enantiomers or diastereomers. Individual stereoisomers of compounds of the present disclosure can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Also, moieties disclosed herein which exist in multiple tautomeric forms include all such forms encompassed by a given tautomeric structure.

Individual atoms in the disclosed compounds may be any isotope of that element. For example hydrogen may be in the form of deuterium.

"Pharmaceutically acceptable" means approved or approvable by a regulatory agency of the Federal or state government or listed in the U.S. Pharmacopoeia or other generally recognized pharmacopoeia for use in animals, and more particularly in humans. It can be material which is not biologically or otherwise undesirable, i.e., the material can be administered to an individual without causing any undesirable biological effects or interacting in a deleterious manner with any of the components of the composition in which it is contained.

The term "pharmaceutically acceptable salt" of a compound means a salt that is pharmaceutically acceptable and that possesses the desired pharmacological activity of the parent compound. Such salts include, for example, acid addition salts and base addition salts.

"Acid addition salts" according to the present disclosure, are formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and the like.

"Base addition salts" according to the present disclosure are formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, ammonia, cyclohexylamine, dicyclohexylamine, and the like. Acceptable inorganic bases include aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature can cause a single crystal form to dominate.

The term "treating" includes the administration of the compounds or agents of the present disclosure to a subject to prevent or delay, to alleviate, or to arrest or inhibit development of the symptoms or conditions associated with fatty acid synthase-associated disorders.

A "therapeutically effective amount" or "pharmaceutically effective amount" means the amount that, when administered to a subject, produces effects for which it is administered. For example, a "therapeutically effective amount," when administered to a subject to inhibit fatty acid synthase activity, is sufficient to inhibit fatty acid synthase activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the present disclosure can be administered. In an exemplary aspect of the present disclosure, to identify subject patients for treatment according to the methods of the present disclosure, accepted screening methods are employed to determine risk factors associated with a targeted or suspected disease or condition or to determine the status of an existing disease or condition in a subject. These screening methods include, for example, conventional workups to determine risk factors that are associated with the targeted or suspected disease or condition. These and other routine methods allow the clinician to select patients in need of therapy using the methods and formulations of the present disclosure.

Chemical names for the compounds of the present disclosure were generated using ChemDraw Ultra version 12.0 (CambridgeSoft Corp., Cambridge Mass.).

FASN Pathway Modulators

As noted above, the present disclosure provides heterocyclic modulators of lipid synthesis and methods of treating conditions characterized by disregulation of a fatty acid synthase pathway, such as viral infections and cancer, by the administration of such compound and combinations of such compounds and other therapeutic agents.

In one aspect, the heterocyclic modulators of lipid synthesis are inhibitors of the fatty acid synthesis pathway. Examples of inhibitors of the fatty acid synthesis pathway that can be used in the methods and compositions of the present disclosure are described below.

In various aspects, the present disclosure provides for compounds of Structure I:

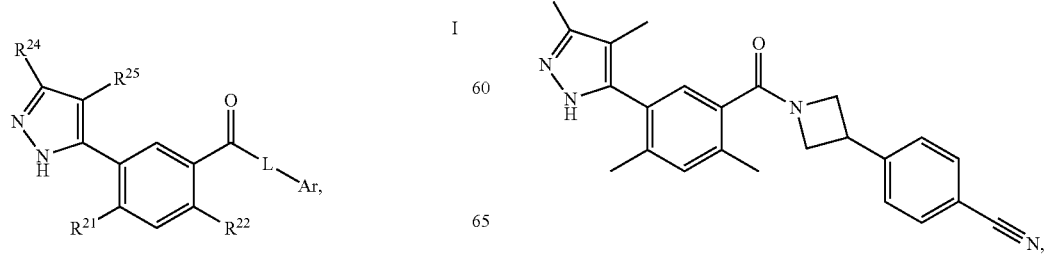

or a pharmaceutically acceptable salt thereof, wherein:

L-Ar is

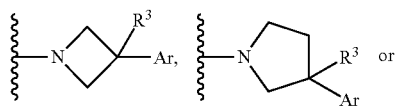

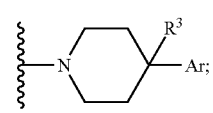

Ar is

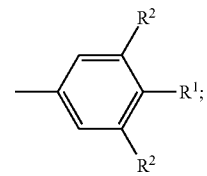

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen;

wherein the compound is not:

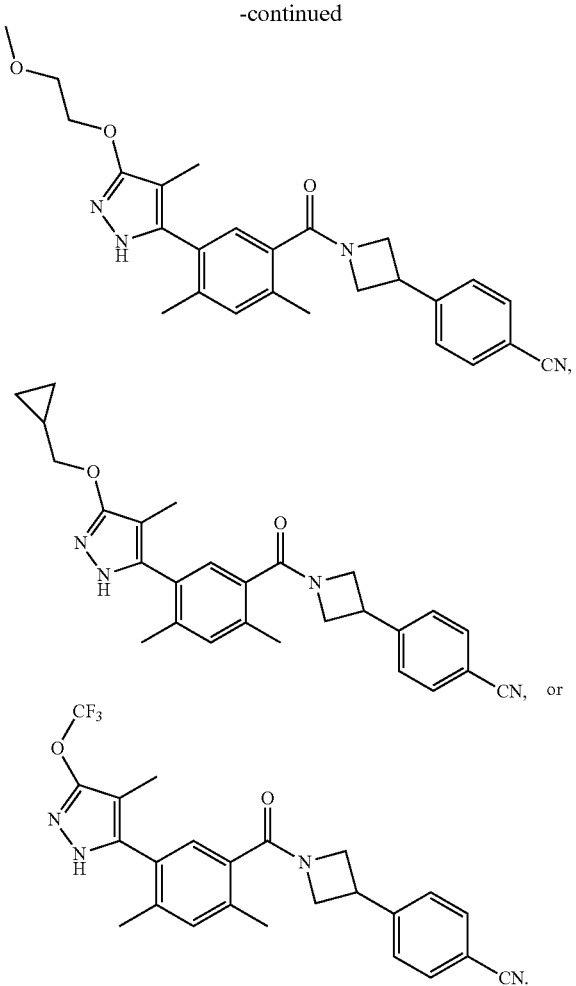

In some embodiments, the present disclosure provides for compounds of Structure I wherein L-Ar is

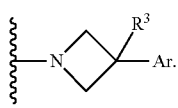

In some embodiments, the present disclosure provides for compounds of Structure I wherein L-Ar is

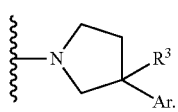

In some embodiments, the present disclosure provides for compounds of Structure I wherein L-Ar is

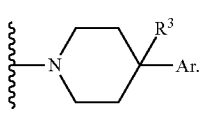

In some embodiments, the present disclosure provides for compounds of Structure I wherein $R^3$ is H.

In some embodiments, the present disclosure provides for compounds of Structure I wherein $R^1$ is —CN or —O—($C_1$-$C_4$ alkyl), wherein when $R^1$ is not —CN, $R^1$ is optionally substituted with one or more halogen.

In some embodiments, the present disclosure provides for compounds of Structure I wherein $R^1$ is —CN.

In some embodiments, the present disclosure provides for compounds of Structure I wherein $R^1$ is —O—($C_1$-$C_4$ alkyl) optionally substituted with one or more halogen.

In some embodiments, the present disclosure provides for compounds of Structure I wherein each $R^2$ is hydrogen.

In some embodiments, the present disclosure provides for compounds of Structure I wherein $R^{21}$ is $C_1$-$C_4$ alkyl.

In some embodiments, the present disclosure provides for compounds of Structure I wherein $R^{22}$ is H or $C_1$-$C_2$ alkyl.

In some embodiments, the present disclosure provides for compounds of Structure I wherein $R^{24}$ is —O—($C_1$-$C_4$ alkyl) optionally substituted with one or more hydroxyl or halogen.

In some embodiments, the present disclosure provides for compounds of Structure I wherein $R^{24}$ is —O—($C_1$-$C_4$ alkyl) optionally substituted with one or more hydroxyl.

In some embodiments, the present disclosure provides for compounds of Structure I wherein $R^{25}$ is —$CH_3$.

Synthesis of Compounds

Also described herein are methods of synthesizing the compounds of the present disclosure. Compounds of the present disclosure can be synthesized according to the Examples provided below. One skilled in the art will recognize that other compounds of structures can be made by modifications to the specifically disclosed schemes employing methods known to those of skill in the art.

Many such techniques are well known in the art. However, many of the known techniques are elaborated in *Compendium of Organic Synthetic Methods* (Vol. 1, 1971; Vol. 2, 1974; Vol. 3, 1977; Vol. 4, 1980; Vol. 5, 1984; and Vol. 6 as well as *March in Advanced Organic Chemistry* (1985); *Comprehensive Organic Synthesis. Selectivity, Strategy & Efficiency in Modern Organic Chemistry*. In 9 Volumes (1993); *Advanced Organic Chemistry Part B: Reactions and Synthesis*, Second Edition (1983); *Advanced Organic Chemistry, Reactions, Mechanisms, and Structure*, Second Edition (1977); *Protecting Groups in Organic Synthesis*, Second Edition; and *Comprehensive Organic Transformations* (1999).

Antiviral Methods of Treatment

In various aspects, the present disclosure provides methods for treating viral infection in a subject, the method comprising administering to a subject in need of such treatment an effective amount of a compound of Structure I.

In various aspects, the disclosure provides methods for treating a viral infection, the method comprising administering the compounds of the present disclosure to a subject in need thereof.

The present disclosure contemplates the treatment of any viral infection that targets the fatty acid synthesis pathway in a host, and in particular by modulating the activity of fatty acid synthase. For example, the present methods can be used to treat influenza infection, adenovirus infection, respiratory syncytial virus infection, poxvirus infection, poliomyelitis infection, hepatitis C infection, yellow fever infection, dengue fever infection, rhinovirus infection, and the like. In various aspects, the present disclosure provides methods for treating hepatitis C infection by administering to the subject one or more compounds disclosed herein.

In various aspects, the compounds of the present disclosure can be used for the treatment of infection of an animal subject, such as a human.

In certain aspects, the compounds of the present disclosure can be used for the inhibition of a host by a respiratory virus. Respiratory viruses are most commonly transmitted by airborne droplets or nasal secretions and can lead to a wide spectrum of illness. Respiratory viruses include the respiratory syncytial virus (RSV), influenza viruses, coronaviruses such as SARS, adenoviruses, parainfluenza viruses and rhinoviruses (HRV).

According to one aspect, the present disclosure can be used to treat infection by HRV. The genus of rhinoviruses is a member of the Picornaviridae family of viruses. Genera within the family include the Genus *Enterovirus, Rhinovirus, Cardiovirus, Aphthovirus, Hepatovirus, Parechovirus, Erbovirus, Kobuvirus, Teschovirus*. Human rhinoviruses (HRV) include the most common viruses that infect humans and can cause the common cold. HRV are lytic in nature. Rhinoviruses have single-stranded positive sense RNA genomes of between 7.2 and 8.5 kb in length. At the 5' end of these genomes is a virus-encoded protein, and like mammalian mRNA, there is also a 3' poly-A tail. The 5'-terminal UMP of the viral RNA is covalently linked to the small viral protein VPg (Paul A V, et al. *Nature* 1998, 393(6682):280-284). The 5'UTR contains two structural elements. One is the 5'-cloverleaf structure involved in the plus-strand RNA synthesis and in the process of switching from translation to replication (Huang H, et al. *Biochemistry* 2001, 40(27):8055-8064). The other is the internal ribosomal entry site (IRES) which promotes translation of the polyprotein. In addition, species-specific internal cis-acting replication elements (cre) have been identified in human enteroviruses (HEV), HRV-A and HRV-B (Gerber K, Wimmer E, Paul A V, *J Virol* 2001, 75(22):10979-10990). The viral particles themselves are not enveloped and are icosahedral in structure. Rhinoviruses also grow best in temperatures between 33-35° C. They are also sensitive to acidic environment.

HRV viral proteins are transcribed as a single long polypeptide, which is cleaved into the viral structural and nonstructural proteins. Rhinoviruses are composed of a capsid that contains four viral proteins VP1, VP2, VP3 and VP4 (Rossmann M, et al. 1985 *Nature* 317 (6033): 145-53; Smith T, et al. 1986, *Science* 233 (4770): 1286-93). The isometric nucleocapsids are 22-40 nm in diameter. VP1, VP2, and VP3 form the major part of the protein capsid. The much smaller VP4 protein has a more extended structure and lies at interface between the capsid and the RNA genome. There are 60 copies of each of these proteins assembled as an icosahedron. Human antibodies that target epitopes lying on the exterior regions of VP1-VP3 play a role in the immune response to HRVs.

HRVs have two general modes of transmission: 1) via aerosols of respiratory droplets and 2) from contaminated surfaces, including direct person-to-person contact. The primary route of entry for rhinoviruses is the upper respiratory tract. Afterwards, an HRV binds to ICAM-1 (Inter-Cellular Adhesion Molecule 1) also known as CD54 (Cluster of Differentiation 54) receptors on respiratory epithelial cells. As the virus replicates and spreads, infected cells release chemokines and cytokines, which in turn activate inflammatory mediators. Infection occurs rapidly, with the rhinovirus adhering to surface receptors within 15 minutes of entering the respiratory tract. The incubation period is generally 8-10 hours before symptoms begin to occur. HRVs are the most frequent cause of infection across all age groups of the human population. Replication is often restricted to the upper respiratory tract leading to self-limited illnesses such as the common cold. However, HRV infections can also exacerbate pre-existing airway disorders, invade the lower respiratory tract and lead to serious complications.

In another aspect, the compounds of the present disclosure can be used for the treatment of infection by the influenza virus by targeting the pathways that the virus relies on for infection or replication. Influenza viruses belong to Orthomyxoviridae family of viruses. This family also includes Thogoto viruses and Dhoriviruses. There are several types and subtypes of influenza viruses known, which infect humans and other species. Influenza type A viruses infect people, birds, pigs, horses, seals and other animals, but wild birds are the natural hosts for these viruses. Influenza type A viruses are divided into subtypes and named on the basis of two proteins on the surface of the virus: hemagglutinin (HA) and neuraminidase (NA). For example, an "H7N2 virus" designates an influenza A subtype that has an HA 7 protein and an NA 2 protein. Similarly an "H5N1" virus has an HA 5 protein and an NA 1 protein. There are 16 known HA subtypes and 9 known NA subtypes. Many different combinations of HA and NA proteins are possible. Only some influenza A subtypes (i.e., H1N1, H1N2, and H3N2) are currently in general circulation among people. Other subtypes are found most commonly in other animal species. For example, H7N7 and H3N8 viruses cause illness in horses, and H3N8 also has recently been shown to cause illness in dogs (see www.cdc.gov/flu/avian/gen-info/flu-viruses.htm).

Antiviral agents which target host cell proteins involved in influenza infection can be used to protect high-risk groups (hospital units, institutes caring for elderly, immuno-suppressed individuals), and on a case by case basis. A potential use for antiviral agents is to limit the spread and severity of the future pandemics whether caused by avian H5N1 or other strains of influenza virus. Avian influenza A viruses of the subtypes H5 and H7, including H5N1, H7N7, and H7N3 viruses, have been associated with high pathogenicity, and human infection with these viruses have ranged from mild (H7N3, H7N7) to severe and fatal disease (H7N7, H5N1). Human illness due to infection with low pathogenicity viruses has been documented, including very mild symptoms (e.g., conjunctivitis) to influenza-like illness. Examples of low pathogenicity viruses that have infected humans include H7N7, H9N2, and H7N2 (see www.cdc.gov/flu/avian % gen-info/flu-viruses.htm).

Influenza B viruses are usually found in humans but can also infect seals. Unlike influenza A viruses, these viruses are not classified according to subtype. Influenza B viruses can cause morbidity and mortality among humans, but in general are associated with less severe epidemics than influenza A viruses. Although influenza type B viruses can cause human epidemics, they have not caused pandemics. (see www.cdc.gov/flu/avian/gen-info/flu-viruses.htm).

Influenza type C viruses cause mild illness in humans and do not cause epidemics or pandemics. These viruses can also infect dogs and pigs. These viruses are not classified according to subtype. (see www.cdc.gov/flu/avian/gen-info/flu-viruses.htm).

Influenza viruses differ from each other in respect to cell surface receptor specificity and cell tropism, however they use common entry pathways. The compounds of the present disclosure advantageously target pathways that are common to multiple viruses giving rise to broader antiviral activity. Thus, the present compounds can also prove useful against unrelated viruses that use similar pathways. For example, the agents can protect airway epithelial cells against a number of different viruses in addition to influenza viruses.

In certain aspects, the compounds of the present disclosure can be used for the treatment of infection by adenoviruses. Most adenoviruses commonly cause respiratory illness; symptoms of respiratory illness caused by adenovirus infection range from the common cold syndrome to pneumonia, croup, and bronchitis. Patients with compromised immune systems are especially susceptible to severe complications of adenovirus infection. Acute respiratory disease (ARD), first recognized among military recruits during World War II, can be caused by adenovirus infections during conditions of crowding and stress. Adenoviruses are medium-sized (90-100 nm), nonenveloped icosohedral viruses containing double-stranded DNA. There are 49 immunologically distinct types (6 subgenera: A through F) that can cause human infections. Adenoviruses are unusually stable to chemical or physical agents and adverse pH conditions, allowing for prolonged survival outside of the body. Some adenoviruses, such as AD2 and Ad5 (species C) use clathrin mediated endocytosis and macropinocytosis for infectious entry. Other adenoviruses, such as Ad3 (species B) use dynamin dependent endocytosis and macropinocytosis for infectious entry.

In certain aspects, the compounds of the present disclosure can be used for the treatment of infection by respiratory syncytial virus (RSV). RSV is the most common cause of bronchiolitis and pneumonia among infants and children under 1 year of age. Illness begins most frequently with fever, runny nose, cough, and sometimes wheezing. During their first RSV infection, between 25% and 40% of infants and young children have signs or symptoms of bronchiolitis or pneumonia, and 0.5% to 2% require hospitalization. Most children recover from illness in 8 to 15 days. The majority of children hospitalized for RSV infection are under 6 months of age. RSV also causes repeated infections throughout life, usually associated with moderate-to-severe cold-like symptoms; however, severe lower respiratory tract disease can occur at any age, especially among the elderly or among those with compromised cardiac, pulmonary, or immune systems. RSV is a negative-sense, enveloped RNA virus. The virion is variable in shape and size (average diameter of between 120 and 300 nm), is unstable in the environment (surviving only a few hours on environmental surfaces), and is readily inactivated with soap and water and disinfectants.

In certain aspects, the compounds of the present disclosure can be used for the treatment of infection by human parainfluenza virus (HPIV). HPIVs are second to respiratory syncytial virus (RSV) as a common cause of lower respiratory tract disease in young children. Similar to RSV, HPIVs can cause repeated infections throughout life, usually manifested by an upper respiratory tract illness (e.g., a cold and/or sore throat). HPIVs can also cause serious lower respiratory tract disease with repeat infection (e.g., pneumonia, bronchitis, and bronchiolitis), especially among the elderly, and among patients with compromised immune systems. Each of the four HPIVs has different clinical and epidemiologic features. The most distinctive clinical feature of HPIV-1 and HPIV-2 is croup (i.e., laryngotracheobronchitis); HPIV-1 is the leading cause of croup in children, whereas HPIV-2 is less frequently detected. Both HPIV-1 and -2 can cause other upper and lower respiratory tract illnesses. HPIV-3 is more often associated with bronchiolitis and pneumonia. HPIV-4 is infrequently detected, possibly because it is less likely to cause severe disease. The incubation period for HPIVs is generally from 1 to 7 days.

HPIVs are negative-sense, single-stranded RNA viruses that possess fusion and hemagglutinin-neuraminidase glycoprotein "spikes" on their surface. There are four serotypes types of HPIV (1 through 4) and two subtypes (4a and 4b). The virion varies in size (average diameter between 150 and 300 nm) and shape, is unstable in the environment (surviving a few hours on environmental surfaces), and is readily inactivated with soap and water.

In various aspects, the compounds of the present disclosure can be used for the treatment of infection by coronavirus. Coronavirus is a genus of animal virus belonging to the family Coronaviridae. Coronaviruses are enveloped viruses with a positive-sense single-stranded RNA genome and a helical symmetry. The genomic size of coronaviruses ranges from approximately 16 to 31 kilobases, extraordinarily large for an RNA virus. The name "coronavirus" is derived from the Latin corona, meaning crown, as the virus envelope appears under electron microscopy to be crowned by a characteristic ring of small bulbous structures. This morphology is actually formed by the viral spike peplomers, which are proteins that populate the surface of the virus and determine host tropism. Coronaviruses are grouped in the order Nidovirales, named for the Latin nidus, meaning nest, as all viruses in this order produce a 3' co-terminal nested set of subgenomic mRNA's during infection. Proteins that contribute to the overall structure of all coronaviruses are the spike, envelope, membrane and nucleocapsid. In the specific case of SARS a defined receptor-binding domain on S mediates the attachment of the virus to its cellular receptor, angiotensin-converting enzyme 2.

In a further embodiment, the disease state associated with dysregulation of the mTOR pathway is a viral infection. In one embodiment, the viral infection is by a virus from the herpesviridae family of viruses. In one embodiment the viral infection is by a herpesviridae virus selected from the group consisting of herpes simplex virus (HSV) types 1 and 2, varicella-zoster virus, cytomegalovirus (CMV), Epstein-Barr virus (EBV), human herpesvirus 6 (variants A and B), human herpesvirus 7, human herpesvirus 8 (Kaposi's sarcoma—associated herpesvirus, KSHV), and cercopithecine herpesvirus 1 (B virus). In one embodiment the viral infection is by a virus selected from human cytomegalovirus and herpes simplex virus-I.

In one embodiment, the viral infection is by a virus from the paramyxoviridae family of viruses. In one embodiment, the viral infection is by a paramyxoviridae virus selected from the group consisting of Respiratory syncytial virus (RSV), mumps, measles, human parainfluenza viruses such as Parainfluenza Virus Type 3 (PIV3), Human metapneumovirus, Hendra virus (HeV), Nipah virus (NiV), and Cedar Virus.

In one embodiment, the viral infection is by a virus from the picornaviridae family of viruses. In one embodiment, the viral infection is by a picornaviridae virus selected from the group consisting of Human rhinovirus 16 (HRV-16), Human enterovirus, Hepatitis A virus, Coxsackie virus (including type A24 variant CA24v), Echovirus, and Poliovirus.

In one embodiment, the viral infection is by a virus from the orthomyxoviridae family of viruses. In one embodiment, the viral infection is by a orthomyxoviridae virus selected from the group consisting of Avian influenza (pathogenic strain (H5N1)), and Swine influenza including influenza C and the subtypes of influenza A known as H1N1, H1N2, H2N1, H3N1, H3N2, and H2N3.

In one embodiment, the viral infection is by a virus from the retroviridae family of viruses. In one embodiment, the viral infection is by a retroviridae virus selected from the group consisting of human immunodeficiency virus (HIV-1).

In one embodiment, the viral infection is by a virus from the papillomaviridae family of viruses. In one embodiment, the viral infection is by a papillomaviridae virus selected from the group consisting of human papillomavirus (HPV).

In one embodiment, the viral infection is by a virus from the adenoviridae family of viruses. In one embodiment, the viral infection is by a adenoviridae virus selected from the group consisting of human adenovirus (Adenovirus serotype 14.)

In one embodiment, the viral infection is by a virus from the poxviridae family of viruses. In one embodiment, the viral infection is by a poxviridae virus selected from the group consisting of Human orthopoxviruses, Monkeypox virus, Variola (VARV), including smallpox (Variola major virus) and Alastrim (Variola minor virus)), Cowpox (CPX), and Vaccinia (VACV or VV) viruses.

In one embodiment, the viral infection is by a virus from the polyomaviridae family of viruses.

In one embodiment, the viral infection is by a virus causing viral hemorrhagic fever. In one embodiment, the virus causing viral hemorrhagic fever is selected from the group consisting of arenaviruses, filoviruses, bunyaviruses, and flaviviruses including Bundibugyo virus (BDBV), Sudan virus (SUDV), Taï Forest virus (TAFV) and Ebola virus (EBOV, formerly Zaire Ebola virus), Marburg, Lassa, Crimean-Congo, Seoul viruses. Lassa fever virus, Lujo virus and Argentine hemorrhagic fever. In one embodiment, the virus causing viral hemorrhagic fever is a South American Haemorrhagic Fever virus selected from the group consisting of Chapare, Guanarito, Junin, Machupo, Sabia, Hantavirus hemorrhagic fever with renal syndrome (HFRS) and hantavirus pulmonary syndrome (HPS).

In one embodiment, the viral infection is by a virus from the flaviviridae family of viruses. In one embodiment, the viral infection is by a flaviviridae virus selected from the group consisting of Yellow fever, tick-borne encephalitis virus (TBEV), Kyasanur Forest disease virus, Omsk hemorrhagic fever virus, hepatitis B virus (HBV), hepatitis C virus (HCV), Dengue viruses (DEN-1, DEN-2, DEN-3 and DEN-4), West Nile virus.

In one embodiment, the viral infection is by a virus from the togaviridae family of viruses. In one embodiment, the viral infection is by a togaviridae virus selected from the group consisting of Eastern Equine Encephalitis virus, Venezuelan equine encephalitis virus, Western equine encephalitis virus, zoonotic alphaviruses (Chikungunya virus, Semliki Forest virus complex), and arbovirus.

In one embodiment, the viral infection is by a virus from the coronaviridae family of viruses. In one embodiment, the viral infection is by a coronaviridae virus selected from the group consisting of a SARS-associated coronavirus (SARS-CoV) and MERS (Middle East Respiratory Syndrome, MERS-CoV).

In one embodiment, the viral infection is by a virus from the bunyaviridae family of viruses. In one embodiment, the viral infection is by a bunyaviridae virus selected from the group consisting of Rift Valley fever.

The present disclosure contemplates the treatment of any viral infection that targets the fatty acid synthesis pathway in a host, and in particular by modulating the activity of fatty acid synthase. For example, the present methods can be used to treat infections caused by Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Borna disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group. Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious ecthyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3. Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection. Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus. Orthopoxvirus, Orthoreovirus. Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group. Pestivirus, Phlebovirus, phocine distemper virus. Picodnavirus, Picornavirus, pig cytomegalovirus—pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1. Polyomavirus muris 1. Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group. Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

Anticancer Activity

In various aspects, the present disclosure provides methods for treating cancer in subject, the method comprising administering to a subject in need of such treatment an effective amount of a compound of Structure I. In further aspects, compounds having Structure I can be used for the manufacture of a medicament for treating cancer.

In certain aspects, the present disclosure provides a method for inhibiting tumor cell growth in a subject, the method comprising administering to a subject in need of such treatment an effective amount of a compound of Structure I. In further aspects, the tumor can be derived from breast, lung, thyroid, lymph node, kidney, ureter, bladder, ovary, teste, prostate, bone, skeletal muscle, bone marrow, stomach, esophagus, small bowel, colon, rectum, pancreas, liver, smooth muscle, brain, spinal cord, nerves, ear, eye, nasopharynx, oropharynx, salivary gland, or heart tissue.

In a further embodiment, the tumor is a cancer selected from the group consisting of breast cancer; antle cell lymphoma; renal cell carcinoma; acute myelogenous leukemia (AML); chronic myelogenous leukemia (CML); diffuse large B cell lymphoma (DLBCL); sarcoma; rhabdomyosarcoma; ovarian cancer; endometrial tumors; non small cell lung carcinoma (NSCLC); small cell, squamous, large cell and adenocarcinoma; lung cancer; colon cancer; colorectal tumors; KRAS-mutated colorectal tumors; gastric carcinomas; hepatocellular tumors; liver tumors; primary melanomas; pancreatic cancer; prostate carcinoma; thyroid carcinoma; follicular thyroid carcinoma; anaplastic large cell lymphoma (ALCL); hamaratomas, angiomyelolipomas, TSC-associated and sporadic lymphangioleiomyomatosis; Cowden's disease (multiple hamaratoma syndrome); sclerosing hemangioma; Peutz-Jeghers syndrome (PJS); head and neck cancer, neurofibromatosis; macular degeneration; macular edema; myeloid leukemia; systemic lupus; and autoimmune lymphoproliferative syndrome (ALPS).

In certain aspects, the present disclosure provides a method for treating pancreatic cancer in a subject, the method comprising administering to a subject in need of such treatment an effective amount of a compound of Structure I.

In certain aspects, the present disclosure provides for a method of treating colon cancer in a subject, the method comprising administering to a subject in need of such treatment an effective amount of a compound of Structure I.

Rapidly proliferating cancer cells activate the fatty acid synthesis pathway to supply the high levels of lipids needed for membrane assembly and oxidative metabolism. (Flavin, R. et al. (2010) *Future Oncology.* 6(4):551-562). Inhibitors of fatty acid synthesis have demonstrated in vivo activity in preclinical cancer models. (Orita, H. et al. (2007) *Clinical Cancer Research.* 13(23):7139-7145 and Puig, T. et al. (2011) *Breast Cancer Research.* 13(6):R131). Additionally, fatty acid synthesis supports new blood vessel formation and inhibitors of this pathway have activity in in vitro models of angiogenesis. (Browne, C. D., et al. (2006) *The FASEB Journal,* 20(12):2027-2035).

Utility in Metabolic Disorders

In various aspects, the compounds of the present disclosure have utility in the treating of metabolic diseases. FASN has been demonstrated to be involved in regulation of glucose, lipids and cholesterol metabolism. Mice with a liver-specific inactivation of FASN have normal physiology unless fed a zero-fat diet, in which case they develop hypoglycemia and fatty liver, both of which are reversed with dietary fat. (Chakravarthy, M. V., et al. (2005) *Cell Metabolism* 1:309-322). Db/+ mice fed a high fructose diet exhibit reduced liver triglyceride levels and improved insulin sensitivity when treated for 28 days with platensimycin, a covealent inhibitor of FASN. (Wu, M. et al. (2011) *PNAS* 108(13):5378-5383). Ambient glucose levels are also reduced in db/db mice following treatment with platensimycin. These results provide evidence that inhibiting FASN can yield therapeutically relevant benefits in animal models of diabetes and related metabolic disorders. Thus the disclosed FASN inhibitors are useful in the treatment of disorders characterized by disregulation in these systems. Without limitation, examples include steatosis and diabetes.

Pharmaceutical Compositions, Formulations, Routes of Administration, and Effective Doses Also provided herein are pharmaceutical compositions comprising the compounds of the present disclosure.

In various aspects, the present disclosure provides pharmaceutical compositions comprising any one of the compounds of Structure I and a pharmaceutically acceptable carrier, excipient, or diluent.

Compounds of the present disclosure can be administered as pharmaceutical compositions including those suitable for oral (including buccal and sub-lingual), rectal, nasal, topical, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., *Pharmaceutical Dosage Forms and Drug Delivery Systems* (Lippencott Williams & Wilkins, Baltimore Md. (1999).

In various aspects, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In another aspect, the pharmaceutical composition is substantially free of preservatives. In another aspect, the pharmaceutical composition can contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)). It will be recognized that, while any suitable carrier known to those of ordinary skill in the art can be employed to administer the pharmaceutical compositions of the present disclosure, the type of carrier will vary depending on the mode of administration.

Compounds can also be encapsulated within liposomes using well-known technology. Biodegradable microspheres can also be employed as carriers for the pharmaceutical compositions of the present disclosure. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

Compounds can be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," *Drug Carriers in Biology and Medicine*, pp. 2.sup.87-341 (Academic Press, 1979).

Microspheres formed of polymers or proteins are well known to those skilled in the art, and can be tailored for passage through the gastrointestinal tract directly into the blood stream. Alternatively, compounds can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intravenous injection, as is well known in the art.

Compounds of the present disclosure can be formulated as a sterile solution or suspension, in suitable vehicles, well known in the art. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington *The Science and Practice of Pharmacy* (20$^{th}$ Ed., Lippincott Williams & Wilkins, Baltimore Md.), the teachings of which are incorporated by reference in their entirety herein.

Combination Therapies

As noted above, the present disclosure provides methods of treating conditions characterized by disregulation of a fatty acid synthase pathway (such as viral infections and cancer) by the administration of a heterocyclic modulator of lipid synthesis in combination with other therapeutic agents.

The choice of agents that can be co-administered with the compounds of the present disclosure can depend, at least in part, on the condition being treated. Agents of particular use in the methods of the present disclosure include, for example, any agent having a therapeutic effect for a viral infection, including, e.g., drugs used to treat inflammatory conditions. For example, in treatments for HRV, one or more conventional anti-inflammatory drugs, such as an NSAID, e.g., ibuprofen, naproxen, acetaminophen, ketoprofen, or aspirin, may be administered with a compound of the present disclosure. In treatments for influenza, one or more conventional influenza antiviral agents, such as amantadine, rimantadine, zanamivir, and oseltamivir, may be administered with a compound of the present disclosure. In treatments for retroviral infections, such as HIV, one or more conventional antiviral agents, such as protease inhibitors (lopinaviriritonavir (Kaletra), indinavir (Crixivan), ritonavir (Norvir), nelfinavir (Viracept), saquinavir hard gel capsules (Invirase), atazanavir (Reyataz), amprenavir (Agenerase), fosamprenavir (Telzir), tipranavir (Aptivus)), reverse transcriptase inhibitors, including non-Nucleoside and Nucleoside/nucleotide inhibitors (AZT (zidovudine, Retrovir), ddI (didanosine, Videx), 3TC (lamivudine, Epivir), d4T (stavudine, Zerit), abacavir (Ziagen), FTC (emtricitabine, Emtriva), tenofovir (Viread), efavirenz (Sustiva) and nevirapine (Viramune)), fusion inhibitors T20 (enfuvirtide, Fuzeon), integrase inhibitors (MK-0518 and GS-9137), and maturation inhibitors (PA-457 (Bevirimat)), may be administered with a compound of the present disclosure. As another example, one or more supplements, such as vitamin C, E or other anti-oxidants, may be administered with a compound of the present disclosure.

In certain aspects, the compounds of the present disclosure can be administered in combination with a known cancer therapeutic agent. For example, the compounds can be administered in combination with paclitaxel (commercially available as Taxol, Bristol-Myers Squibb), doxorubicin (also known under the trade name Adriamycin), vincristine (known under the trade names Oncovin, Vincasar PES, and Vincrex), actinomycin D, altretamine, asparaginase, bleomycin, busulphan, cabazitaxel, capecitabine, carboplatin, carmustine, chlorambucil, cisplatin, cyclophosphamide, cytarabine, dacarbazine, daunorubicin, docetaxel, epirubicin, etoposide, fludarabine, fluorouracil, gemcitabine, hydroxyurea, idarubicin, ifosfamide, irinotecan, lomustine, melphalan, mercaptopurine, methotrexate, mitomycin, mitozantrone, oxaliplatin, procarbazine, steroids, streptozocin, taxotere, tamozolomide, thioguanine, thiotepa, tomudex, topotecan, treosulfan, UFT (uracil-tegufur), vinblastine, vindesine, agents targeting immune modulators such as PD-1, PDL-1, and IDO1, e.g. nivolumab, pembrolizumab, MPDL3280A, and MED14736; agents targeting DNA repair deficiency, e.g. olaparib; agents targeting receptor tyrosine kinases such as EGFR, ERBB2, c-MET, VEGFR2, and IGFR1, e.g. erlotinib, necitumumab, traztuzamab, pertuzamab, lapatinib, crizotinib, cabozantinib, onartuamab, ramucirumab, or bevacizumab; agents tarting hormone receptors such as the androgen and estrogen receptors, e.g. enzalutamide, abiraterone, or tamoxifen; agents targeting the MAP kinase or PI3K-AKT pathways, e.g. cobimetinib, vemurafenib, and everolimus; Her2 (ErbB2) pathway blockers such as lapatinib, trastuzumab, and Kadyzla; mTOR blockers such as ralapogs (eg. sirolimus); mTORC1/mTORC1 inhibitors; Angiogenesis or VEGFR pathway blockers such as avastin, nexavar or sutent; Aromatase modulators such as exemtesane or femora; Androgen signaling modulators such as enzalutamide, bicalutamide; and B-RAF blockers such as Tafinlar or Zelboraf, or the like.

Methods of treating comprising administering combinations of a compound of the present disclosure (a fatty acid synthesis pathway inhibitor, e.g., an inhibitor or FASN gene expression or FASN protein activity) with one or more other therapeutic agents may comprise various molar ratios of the two therapeutic agents. For example, molar ratios of about 99:1 to about 1:99 of a fatty acid synthesis pathway inhibitor, e.g., an inhibitor of FASN gene expression or FASN protein activity, to the other therapeutic agent can be used. In some subset of the aspects, the range of molar ratios of the fatty acid synthesis pathway inhibitor, e.g., an inhibitor of FASN gene expression or FASN protein activity, to the other therapeutic agent is selected from about 80:20 to about 20:80; about 75:25 to about 25:75; about 70:30 to about 30:70; about 66:33 to about 33:66; about 60:40 to about 40:60; about 50:50; and about 90:10 to about 10:90. In other aspects, the molar ratio of the fatty acid synthesis pathway inhibitor, e.g., an inhibitor of FASN gene expression or FASN protein activity, to the other therapeutic agent can be about 1:9, and in another aspect can be about 1:1. The two therapeutic agents can be formulated together in the same dosage unit, e.g., in one cream, suppository, tablet, capsule, or packet of powder to be dissolved in a beverage, or each therapeutic agent can be formulated in separate dosage units, e.g., two creams, suppositories, tablets, two capsules, a tablet and a liquid for dissolving the tablet, an aerosol spray a packet of powder and a liquid for dissolving the powder, etc.

EXAMPLES

Example 1

Synthesis of Compounds of the Present Disclosure

General:

All reactions and manipulations described were carried out in well ventilated fume-hoods. Operations and reactions carried out at elevated or reduced pressure were carried out behind blast shields. Abbreviations: ACN, acetonitrile; AcOH, acetic acid; AIBN, azobisisobutyronitrile; BF$_3$-Et$_2$O, boron trifluoride diethyl etherate; (Boc)$_2$O, di-tert-butyl dicarbonate; BuLi, butyl lithium; CDI, 1,1'-Carbonyldiimidazole; DBU, 1,8-Diazabicyclo[5.4.0]undec-7-ene; DCE, 1,2-dichloroethane; DCM, dichloromethane or methylene chloride; DIEA, N,N-Diisopropylethylamine; DMA, N,N-dimethylacetamide; DMAP, 4-dimethylaminopyridine; DME, 1,2-dimethoxyethane; DMEDA-N,N'-dimethylethylenediamine; DMF, N,N-dimethylformamide; DMSO, dimethylsulfoxide; DPPP, 1,3-bis(diphenylphosphino)propane; EDC, 1-ethyl-3-(3-dimethylaminopropyl)carbodiimide; EDCI, 1-ethyl-3-(3-dimethylaminopropyl)carbodiimide hydrochloride; EtOAc, ethyl acetate; EtOH, Ethanol; HATU, 2-(1H-7-Azabenzotriazol-1-yl)-1,1,3,3-tetramethyl uronium hexafluorophosphate; HBTU, O-Benzotriazole-N,N,N',N'-tetramethyl-uronium-hexafluoro-phosphate or 2-(1H-Benzotriazole-1-yl)-1,1,3,3-tetramethylaminium hexafluorophosphate; HMPA, hexamethylphosphoramide; HOAc, acetic acid; HOBT, 1-Hydroxybenzotriazole; LDA, lithium diisopropylamine; m-CPBA, 3-chloroperbenzoic acid; MeOH, methanol; MsCl, methanesulfonyl chloride; MsOH, methanesulfonic acid; NaHMDS, sodium hexamethyldisilazane, NBS, N-bromosuccinimide; NCS, N-chlorosuccinimide; NIS, N-iodosuccinimide; Pd(dppf)Cl$_2$, [1,1'-Bis(diphenylphosphino)ferrocene]dichloropalladium(II);
PE, petroleum ether; PPA, polyphosporic acid; PTAT, phenyltrimethylammonium tribromide; PTSA, p-toluenesulfonic acid; Py, pyridine; Pyr, pyridine; TBAF, tetrabutylammonium fluoride; TEA, triethylamine; TFA, trifluoroacetic acid; TFAA, trifluoroacetic anhydride; THF, tetrahydrofuran; TMSCl, chlorotrimethylsilane; TMSCN, trimethylsilyl cyanide; TsOH, p-toluenesulfonic acid.

Synthesis of MonoMethyl Ester Intermediate

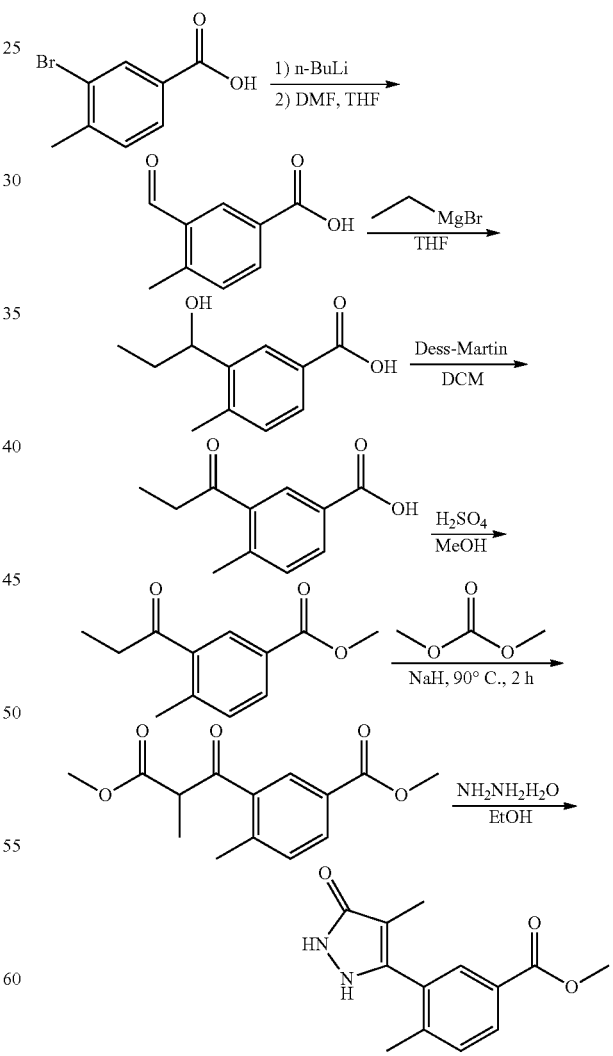

Step 1.

Into a 3000-mL 3-necked round-bottom flask purged and maintained with an inert atmosphere of nitrogen, was placed a solution of 3-bromo-4-methylbenzoic acid (100 g, 465 mmol, 1.00 equiv) in tetrahydrofuran (1500 mL). To this was added n-BuLi (2.5 M in THF) (411 mL, 1023 mmol, 2.20 equiv) dropwise at −78° C. and stirred for 30 min. N,N-dimethylformamide (101 g, 1.38 mol, 3.00 equiv) was added to the reaction at −78° C. The resulting solution was stirred for 30 min at −78° C. in a liquid nitrogen bath, then quenched with 1000 mL of water. The aqueous layers was washed with 1000 mL of ethyl acetate and the pH value of the solution was adjusted to 3-4 with 6N hydrogen chloride. The solids were collected by filtration and dried in an oven. This resulted in 45 g (59%) of 3-formyl-4-methylbenzoic acid as a yellow solid.

Step 2.

Into a 2000-mL round-bottom flask purged and maintained with an inert atmosphere of nitrogen, was placed a solution of 3-formyl-4-methylbenzoic acid (40 g, 243.67 mmol, 1.00 equiv) in THF (1000 mL). To this was added bromo(ethyl)magnesium (244 mL, 3N in ether, 3.00 equiv) dropwise at 0° C. The resulting solution was stirred for 2-3 h at 20° C., then quenched with 500 mL of NH$_4$Cl (sat.). The pH value of the solution was adjusted to 4-5 with hydrogen chloride (6 mol/L). The aqueous phase was extracted with 2×500 mL of ethyl acetate and the combined organic layers were dried over anhydrous sodium sulfate and concentrated under vacuum. This resulted in 50 g (crude) of 3-(1-hydroxypropyl)-4-methylbenzoic acid as a yellow solid.

Step 3.

Into a 2000-mL round-bottom flask, was placed a solution of 3-(1-hydroxypropyl)-4-methylbenzoic acid (50 g (crude), 1.00 equiv) in dichloromethane (1000 mL), Dess-Martin (131 g, 309.28 mmol, 1.20 equiv). The resulting solution was stirred for 2 h at 25° C., then quenched with 500 mL of 2M Na$_2$S$_2$O$_3$(aq.). The solid was filtered out, the aqueous phase was extracted with 2×500 mL of ethyl acetate and concentrated under vacuum. This resulted in 45 g (crude) of 4-methyl-3-propanoylbenzoic acid as a yellow solid.

Step 4.

Into a 2000-mL round-bottom flask purged and maintained with an inert atmosphere of nitrogen, was placed a solution of 4-methyl-3-propanoylbenzoic acid (45 g (crude), 1.00 equiv) in methanol (1000 mL). To this was added sulfuric acid (45.9 g, 468.4 mmol, 2.00 equiv) dropwise. The resulting solution was stirred for 4 h at 80° C. in an oil bath, then concentrated under vacuum. The reaction was quenched with 500 mL of water/ice. The aqueous phase was extracted with 2×500 mL of ethyl acetate. The combined organic layers were washed with 1×200 mL of sodium bicarbonate (sat.), 2×200 mL of brine, dried over anhydrous sodium sulfate and concentrated under vacuum. The residue was applied onto a silica gel column with ethyl acetate/petroleum ether (1/50). This resulted in 22 g (46%) of methyl 4-methyl-3-propanoylbenzoate as a light yellow solid.

Step 5.

To a solution of methyl 4-methyl-3-propanoylbenzoate (5.0 g, 24.24 mmol, 1.00 equiv) in dimethyl carbonate (70 mL) was added sodium hydride (60%) (1.5 g, 62.50 mmol, 1.50 equiv) in portion at 0° C. and stirred for 2.0 h at 90° C. under nitrogen. The reaction was then quenched with 50 mL of NH$_4$Cl (sat.) and extracted with 3×100 mL of ethyl acetate. The organic phase was washed with 2×100 mL of brine and dried over anhydrous sodium sulfate, then concentrated under vacuum to afford 6.8 g (crude) of methyl 3-(3-methoxy-2-methyl-3-oxopropanoyl)-4-methylbenzoate as yellow oil.

Step 6.

To a solution of methyl 3-(3-methoxy-2-methyl-3-oxopropanoyl)-4-methylbenzoate (3.3 g, 12.49 mmol, 1.00 equiv) in ethanol (30 mL) was added NH$_2$NH$_2$.H$_2$O (98%) (1.33 g, 26.66 mmol, 2.00 equiv). The resulting solution was stirred for 4.0 h at reflux, then concentrated under vacuum. The residue was purified by a silica gel chromatography with CH$_2$Cl$_2$/MeOH (50/1-40/1) as eluent to furnish 1.8 g (59%) of methyl 4-methyl-3-(4-methyl-5-oxo-2,5-dihydro-1H-pyrazol-3-yl)benzoate as a light yellow solid.

Synthesis of Compound 1

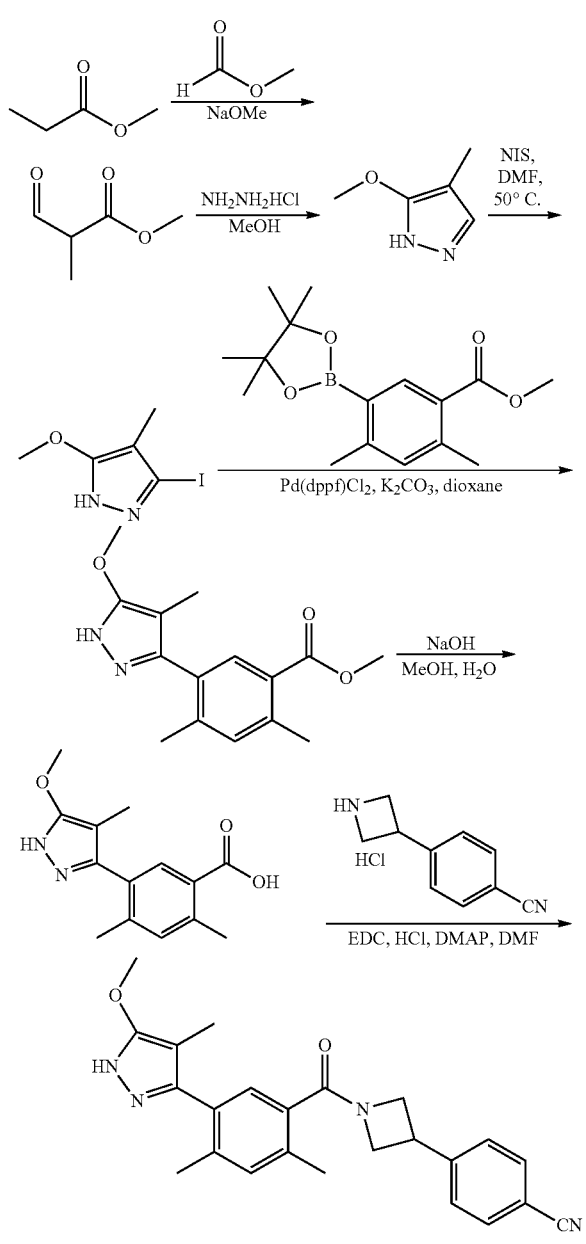

Step 1.

To a solution of methyl propanoate (30 g, 340.50 mmol, 1.00 equiv) in methyl formate (60 mL) was added methoxysodium (22.1 g, 409.08 mmol, 1.20 equiv). The resulting solution was stirred overnight at 25° C. The residue was applied onto a silica gel column with EtOAc:MeOH (10:1) as eluent to yield 3 g (8%) of methyl 2-methyl-3-oxopropanoate as yellow oil.
Step 2.

To a solution of methyl 2-methyl-3-oxopropanoate (5 g, 43.06 mmol, 1.00 equiv) in methanol (10 mL) was added hydrazine hydrochloride (3.52 g, 51.38 mmol, 1.20 equiv). The resulting solution was stirred for 3 h at 60° C. and then concentrated under vacuum. The pH value of the solution was adjusted to 8 with 10% sodium bicarbonate (aq.). The aqueous phase was extracted with 3×30 mL of ethyl acetate and the combined organic layers were washed with 3×30 mL of brine, dried over anhydrous sodium sulfate and concentrated under vacuum. The residue was applied onto a silica gel column with ethyl acetate/petroleum ether (1:1) as eluent to furnish 1.56 g (32%) of 3-methoxy-4-methyl-1H-pyrazole as a yellow solid.
Step 3.

To a solution of 5-methoxy-4-methyl-1H-pyrazole (1.56 g, 13.91 mmol, 1.00 equiv) in N,N-dimethylformamide (20 mL) was added NIS (3.76 g, 16.71 mmol, 1.20 equiv). The resulting solution was stirred overnight at 50° C. and then quenched with 10 mL of water. The aqueous phase was extracted with 3×50 mL of ethyl acetate and the combined organic layers were washed with 2×50 mL of brine, dried over anhydrous sodium sulfate and concentrated under vacuum. The residue was applied onto a silica gel column with ethyl acetate/petroleum ether (1:8) as eluent to afford 1.54 g (47%) of 3-iodo-5-methoxy-4-methyl-1H-pyrazole as a yellow solid.
Step 4.

To a solution of methyl 2,4-dimethyl-5-(tetramethyl-1,3,2-dioxaborolan-2-yl)benzoate (2.25 g, 7.75 mmol, 1.00 equiv) in dioxane (25 mL) was added Pd(dppf)Cl$_2$.CH$_2$Cl$_2$ (530 mg, 0.10 equiv), 3-iodo-5-methoxy-4-methyl-1H-pyrazole (1.54 g, 6.47 mmol, 1.20 equiv) and K$_2$CO$_3$ (2 mol/L) (16.2 mL, 5.00 equiv). The resulting solution was stirred overnight at 80° C. under nitrogen, then quenched with 10 mL of water. The aqueous phase was extracted with 3×40 mL of ethyl acetate and the combined organic layers were washed with 2×20 mL of brine, dried over anhydrous sodium sulfate and concentrated under vacuum. The residue was applied onto a silica gel column with ethyl acetate/petroleum ether (1:3) as eluent to yield 1.8 g (85%) of methyl 5-(3-methoxy-4-methyl-1H-pyrazol-5-yl)-2,4-dimethylbenzoate as brown oil.
Step 5.

To a solution of methyl 5-(3-methoxy-4-methyl-1H-pyrazol-5-yl)-2,4-dimethylbenzoate (1.8 g, 6.56 mmol, 1.00 equiv) in methanol (20 mL) was added a solution of sodium hydroxide (1.31 g, 32.75 mmol, 5.00 equiv) in water (10 mL). The resulting solution was stirred for 1 h at 60° C. The resulting mixture was concentrated under vacuum and the pH value of the solution was adjusted to 5 with hydrogen chloride (2 mol/L). The solids were collected by filtration. This resulted in 1.2 g (70%) of 5-(3-methoxy-4-methyl-1H-pyrazol-5-yl)-2,4-dimethylbenzoic acid as a off-white solid.
Step 6.

To a solution of 5-(3-methoxy-4-methyl-1H-pyrazol-5-yl)-2,4-dimethylbenzoic acid (500 mg, 1.92 mmol, 1.00 equiv) in N,N-dimethylformamide (10 mL) was added EDC.HCl (738.5 mg, 3.85 mmol, 2.00 equiv), 4-dimethylaminopyridine (469.2 mg, 3.84 mmol, 2.00 equiv) and 4-(azetidin-3-yl)benzonitrile hydrochloride (447.7 mg, 2.30 mmol, 1.20 equiv). The resulting solution was stirred overnight at 25° C., then quenched with 10 mL of water. The aqueous phase was extracted with 3×50 mL of ethyl acetate and the combined organic layers were washed with 2×50 mL of brine, dried over anhydrous sodium sulfate and concentrated under vacuum. The residue was applied onto a silica gel column with ethyl acetate as eluent to furnish 237.3 mg (31%) of 4-(1-[[5-(3-methoxy-4-methyl-1H-pyrazol-5-yl)-2,4-dimethylphenyl]carbonyl]azetidin-3-yl)benzonitrile (Compound 1) as a white solid. LC-MS: (ES, m/z): [M+H]$^+$ 401. H-NMR: (400 MHz, CD$_3$OD, ppm): δ 7.768-7.748 (2H, m), 7.592-7.572 (2H, m), 7.300 (1H, s), 7.228 (1H, s), 4.661-4.616 (1H, m), 4.495-4.439 (1H, m), 4.250-4.210 (1H, m), 4.133-4.031 (2H, m), 3.933 (3H, s), 2.444 (3H, s), 2.244 (3H, s), 1.793 (3H, s).

Synthesis of Compound 2

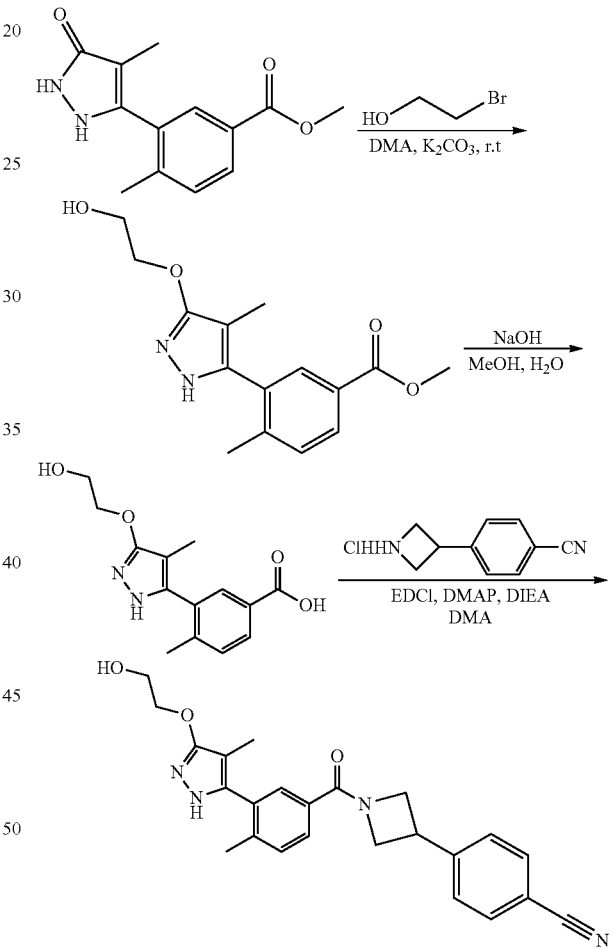

Step 1.

To a solution of methyl 4-methyl-3-(4-methyl-5-oxo-2,5-dihydro-1H-pyrazol-3-yl)benzoate (40 g, 163 mmol, 1.00 equiv) in DMA (800 mL) was added potassium carbonate (112 g, 813 mmol, 5.00 equiv) and 2-bromoethan-1-ol (141 g, 1138 mmol, 7.00 equiv). The mixture was stirred for 4 h at 25° C., then diluted with 1000 mL of H$_2$O. The aqueous phase was extracted with 5×1000 mL of ethyl acetate and the combined organic layers were washed with 2×1000 mL of brine, dried over anhydrous sodium sulfate and concentrated under vacuum. The residue was applied onto a silica gel column with ethyl acetate/petroleum ether (1:10-1:1) as eluent to yield 30 g (64%) of methyl 3-(3-(2-hydroxyethoxy)-4-methyl-1H-pyrazol-5-yl)-4-methylbenzoate as light yellow oil.

Step 2.

To a solution of methyl 3-(3-(2-hydroxyethoxy)-4-methyl-1H-pyrazol-5-yl)-4-methylbenzoate (30 g, 103 mmol, 1.00 equiv) in methanol (500 mL) was added a solution of sodium hydroxide (41 g, 1025 mmol, 10.0 equiv) in water (300 mL). The mixture was stirred for 2 h at room temperature. The resulting mixture was concentrated under vacuum and the pH value of the solution was adjusted to 4-5 with hydrogen chloride (2 mol/L). The solids were collected by filtration. This resulted in 20 g (71%) of 3-(3-(2-hydroxyethoxy)-4-methyl-1H-pyrazol-5-yl)-4-methylbenzoic acid as a light yellow solid.

Step 3.

To a solution of 3-(3-(2-hydroxyethoxy)-4-methyl-1H-pyrazol-5-yl)-4-methylbenzoic acid (20.0 g, 72.5 mmol, 1.00 equiv) in DCM (500 mL) was added EDCI (16.7 g, 87.0 mmol, 1.20 equiv), 4-dimethylaminopyridine (1.77 g, 14.5 mmol, 0.20 equiv), DIEA (23.4 g, 181 mmol, 2.50 equiv) and 4-(azetidin-3-yl)benzonitrile hydrochloride (15.5 g, 79.7 mmol, 1.10 equiv). The resulting solution was stirred for overnight at room temperature. The resulting solution was diluted with 500 mL of H₂O. The resulting solution was extracted with 3×500 mL of ethyl acetate and the combined organic layers were washed with 2×500 mL of NH4Cl (sat.), 2×500 mL of brine and dried over anhydrous sodium sulfate and concentrated under vacuum. The residue was purified by a silica gel chromatography with CH2Cl2/MeOH (50/1-30/1) as eluent to furnish 21.0 g (67%) of 4-(1-(3-(3-(2-hydroxyethoxy)-4-methyl-1H-pyrazol-5-yl)-4-methylbenzoyl)azetidin-3-yl)benzonitrile (Compound 2) as a white solid.

Synthesis of Compound 3

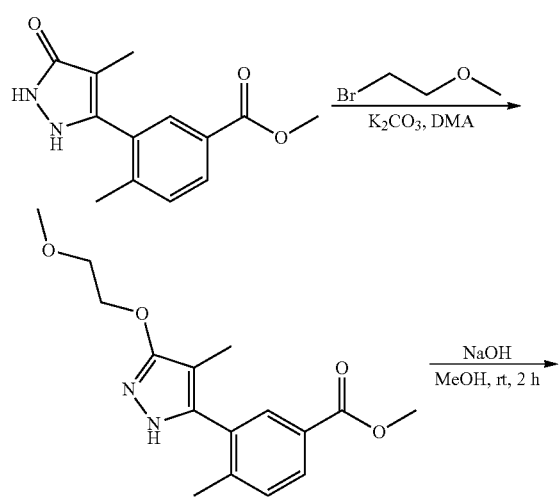

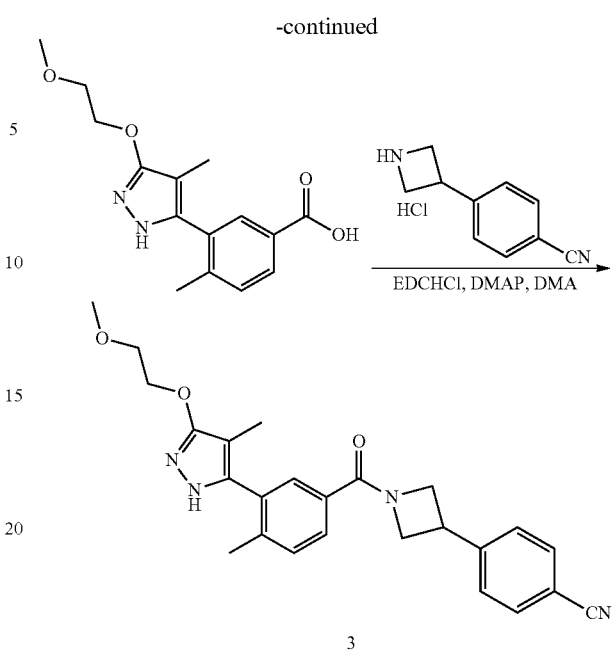

3

Step 1.

To a solution of methyl 4-methyl-3-(4-methyl-5-oxo-2,5-dihydro-1H-pyrazol-3-yl)benzoate (300.0 mg, 1.22 mmol, 1.00 equiv) in DMA (10 mL) was added K₂CO₃ (841.5 mg, 6.10 mmol, 5 equiv) and 1-bromo-2-methoxyethane (1.178 g, 8.54 mmol, 7 equiv). The resulting solution was stirred for 4 h at room temperature. The resulting solution was diluted with 20 mL of H₂O and extracted with 3×50 mL of ethyl acetate. The combined organic layers were dried over anhydrous sodium sulfate and concentrated under vacuum. The crude product (300 mg) was purified by Prep-HPLC with the following conditions (Prep-HPLC-020): Column, Sunfire Prep C18 OBD Column, 19*150 mm 5 um 10 nm; mobile phase, Water with 10 mmol NH₄HCO₃ and ACN (30.0% ACN up to 65.0% in 8 min, up to 95.0% in 1 min, down to 30.0% in 1 min); Detector, waters2489 254&220 nm. This resulted in 130.0 mg (35%) of methyl 3-(3-(2-methoxyethoxy)-4-methyl-1H-pyrazol-5-yl)-4-methylbenzoate as light yellow oil.

Step 2.

To a solution of methyl 3-(3-(2-methoxyethoxy)-4-methyl-1H-pyrazol-5-yl)-4-methylbenzoate (130.0 mg, 0.43 mmol, 1.00 equiv) in methanol (5 m L) was added a solution of sodium hydroxide (171.0 mg, 4.28 mmol, 10.00 equiv) in water (5 mL). The resulting solution was stirred for 2 h at room temperature. The mixture was concentrated under vacuum and the pH value of the resulting solution was adjusted to 5 with hydrogen chloride (2 mol/L). The solids were collected by filtration. This resulted in 105.0 mg (85%) of 3-(3-(2-methoxyethoxy)-4-methyl-1H-pyrazol-5-yl)-4-methylbenzoic acid as a white solid.

Step 3.

To a solution of 3-(3-(2-methoxyethoxy)-4-methyl-1H-pyrazol-5-yl)-4-methylbenzoic acid (100.0 mg, 0.34 mmol, 1.00 equiv) in N,N-dimethylformamide (10 mL) was added 4-(azetidin-3-yl)benzonitrile hydrochloride (80.3 mg, 0.41 mmol, 1.20 equiv), EDCI (132.4 mg, 0.69 mmol, 2.00 equiv) and 4-dimethylaminopyridine (84.1 mg, 0.69 mmol, 2.00 equiv). The mixture was stirred for 2 h at room temperature. The resulting solution was diluted with 20 mL of H₂O and extracted with 3×50 mL of ethyl acetate, then the organic layers combined and dried over anhydrous sodium sulfate and concentrated under vacuum. The crude product (200 mg) was purified by Prep-HPLC with the following conditions (Prep-HPLC-020): Column, Sunfire Prep C18 OBD Column, 19*150 mm 5 um 10 nm; mobile phase, Water with 10 mmol NH$_4$HCO$_3$ and ACN (35.0% ACN up to 65.0% in 8 min, up to 95.0% in 1 min, down to 35.0% in 1 min); Detector, waters2489 254&220 nm. This resulted in 102.1 mg (69%) of 4-[1-([3-[1-(2-methoxyethyl)-4-methyl-5-oxo-2,5-dihydro-1H-pyrazol-3-yl]-4-methylphenyl]carbonyl)azetidin-3-yl]benzonitrile (Compound 3) as a white solid. LC-MS: (ES, m/z): [M+H]$^+$ 431. H-NMR: (300 MHz, CD$_3$OD, ppm): δ 7.64-7.56 (3H, m), 7.49-7.45 (3H, m), 7.34 (1H, d, J=8.1 Hz), 4.75-4.68 (2H, m), 4.55-4.49 (1H, m), 4.36-3.92 (5H, m), 3.82-3.56 (2H, m), 3.20 (3H, m), 2.18 (3H, s), 1.70 (3H, s).

Synthesis of Compound 4

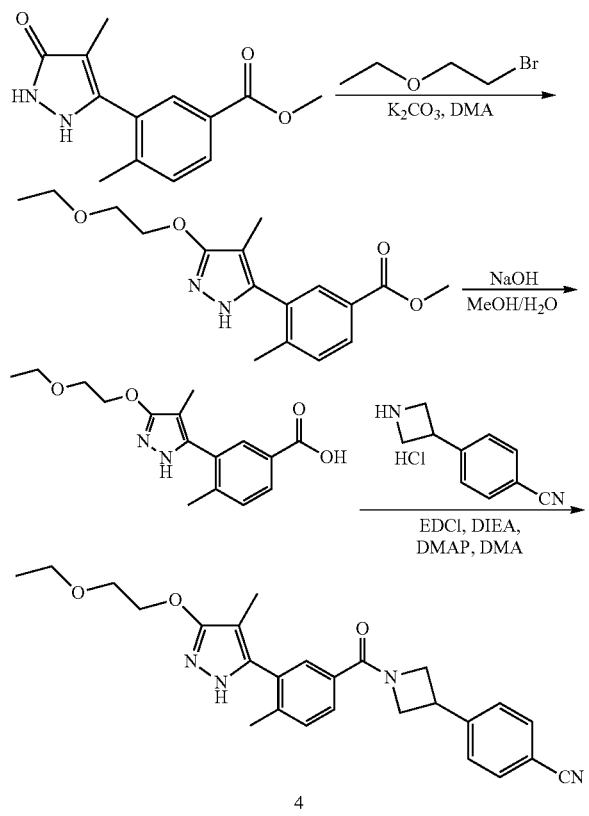

Step 1.

To a solution of methyl 4-methyl-3-(4-methyl-5-oxo-2,5-dihydro-1H-pyrazol-3-yl)benzoate (600 mg, 2.44 mmol, 1.00 equiv) in DMA (20 mL) was added 1-bromo-2-ethoxyethane (2.60 g, 17.1 mmol, 7 equiv) and potassium carbonate (1.68 g, 12.2 mmol, 5 equiv). The resulting solution was stirred for 4 h at 25° C., then diluted with 50 mL of H$_2$O. The aqueous extracted with 3×50 mL of ethyl acetate and the combined organic layers were washed with 2×50 mL of brine, dried over anhydrous sodium sulfate and concentrated under vacuum. The crude product (600 mg) was purified by Prep-HPLC with the following conditions (Prep-HPLC-020): Column, Sunfire Prep C18 OBD Column, 19*150 mm 5 um 10 nm; mobile phase, water with 0.05% TFA and ACN (35.0% ACN up to 75.0% in 9 min, up to 95.0% in 1 min, down to 35.0% in 1 min); Detector, waters2489 254&220 nm. This resulted in 320 mg (41%) of methyl 3-(3-(2-ethoxyethoxy)-4-methyl-1H-pyrazol-5-yl)-4-methylbenzoate as a white solid.

Step 2.

To a solution of methyl 3-(3-(2-ethoxyethoxy)-4-methyl-1H-pyrazol-5-yl)-4-methylbenzoate (350 mg, 1.10 mmol, 1.00 equiv) in methanol (10 mL) was added a solution of sodium hydroxide (440 mg, 11.00 mmol, 10.00 equiv) in water (5 mL). The resulting solution was stirred for 2.0 h at 25° C. The mixture was concentrated under vacuum and the pH value of the solution was adjusted to 5.0 with hydrogen chloride (2 mol/L). The solids were collected by filtration. This resulted in 300 mg (90%) of 3-(3-(2-ethoxyethoxy)-4-methyl-1H-pyrazol-5-yl)-4-methylbenzoic acid as a white solid.

Step 3.

To a solution of 3-(3-(2-ethoxyethoxy)-4-methyl-1H-pyrazol-5-yl)-4-methylbenzoic acid (200 mg, 0.66 mmol, 1.00 equiv) in DMA (10 mL) was added EDCI (253 mg, 1.32 mmol, 2.00 equiv), 4-dimethylaminopyridine (12 mg, 0.10 mmol, 0.15 equiv), DIEA (254 mg, 1.97 mmol, 3.00 equiv) and 4-(azetidin-3-yl)benzonitrile hydrochloride (153 mg, 0.79 mmol, 1.20 equiv). The resulting solution was stirred for 3 h at 25° C., then quenched with 30 mL of NH$_4$Cl (sat.). The aqueous phase was extracted with 3×30 mL of ethyl acetate and the combined organic layers were dried over anhydrous sodium sulfate, then concentrated under vacuum. The crude product (200 mg) was purified by Prep-HPLC with the following conditions (Prep-HPLC-020): Column, Sunfire Prep C18 OBD Column, 19*150 mm 5 um 10 nm; mobile phase, Water with 10 mmol NH$_4$HCO$_3$ and ACN (25.0% ACN up to 75.0% in 8 min); Detector, Waters 2489 254&220 nm. This resulted in 142.1 mg (49%) of 4-(1-(3-(3-(2-ethoxyethoxy)-4-methyl-1H-pyrazol-5-yl)-4-methylbenzoyl)azetidin-3-yl)benzonitrile (Compound 4) as a white solid. LC-MS: (ES, m/z): [M+H]$^+$ 445. H-NMR: (300 Hz. CD$_3$OD, ppm): δ 7.74 (2H, m), 7.76 (1H, d, J=8.4 Hz), 7.75 (3H, m), 7.74 (1H, d, J=8.1 Hz), 4.83 (1H, m), 4.43 (1H, m), 4.33 (1H, m), 4.23 (2H, m), 4.15 (1H, m), 4.06 (1H, m), 3.82 (2H, m), 3.62 (2H, m), 2.31 (3H, s), 1.83 (3H, s), 1.24 (3H, t).

Synthesis of Compound 5

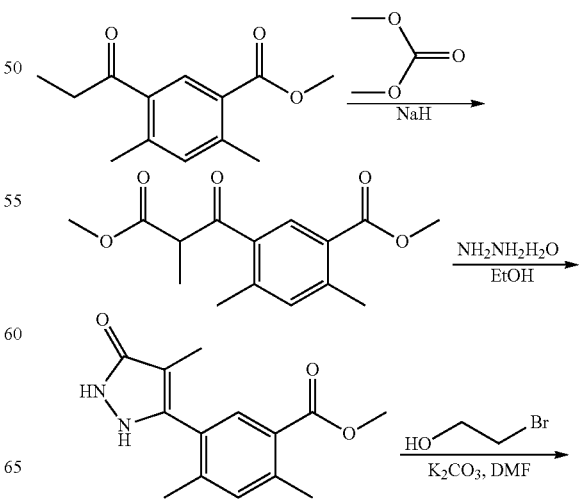

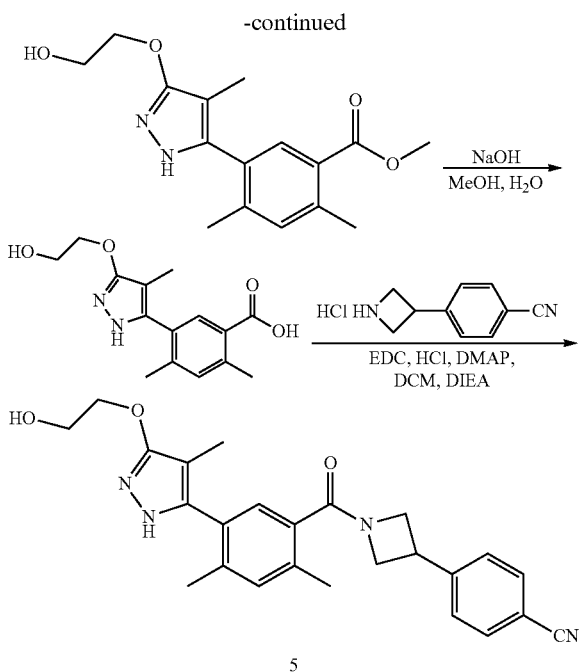

Step 1.

To a solution of methyl 2,4-dimethyl-5-propanoylbenzoate (400 mg, 1.82 mmol, 1.00 equiv) in dimethyl carbonate (5 mL) was added sodium hydride (290 mg, 7.25 mmol, 4.00 equiv, 60%) in portions at 0-5° C. The resulting solution was stirred for 2 h at 80° C., then quenched with 2 mL of water. The resulting solution was diluted with 20 mL of ethyl acetate, then was washed with 2×10 mL of brine and dried over anhydrous sodium sulfate and concentrated under vacuum. This resulted in 400 mg (crude) of methyl 5-(3-methoxy-2-methyl-3-oxopropanoyl)-2,4-dimethylbenzoate as brown oil.

Step 2.

To a solution of methyl 5-(3-methoxy-2-methyl-3-oxopropanoyl)-2,4-dimethylbenzoate (1 g, 3.59 mmol, 1.00 equiv) in ethanol (20 mL) was added hydrazine hydrate (720 mg, 14.38 mmol, 4.00 equiv). The resulting solution was stirred for 3 h at 80° C. in an oil bath. After some solvent was moved, the precipitating solids were collected by filtration to yield 700 mg (75%) of methyl 2,4-dimethyl-5-(4-methyl-5-oxo-2,5-dihydro-1H-pyrazol-3-yl)benzoate as a yellow solid.

Step 3.

To a solution of methyl 2,4-dimethyl-5-(4-methyl-5-oxo-2,5-dihydro-1H-pyrazol-3-yl)benzoate (700 mg, 2.69 mmol, 1.00 equiv) in N,N-dimethylformamide (10 mL) was added potassium carbonate (483 mg, 3.49 mmol, 1.30 equiv) and 2-bromoethan-1-ol (434 mg, 3.47 mmol, 1.30 equiv). The resulting solution was stirred for 1 overnight at room temperature, then was diluted with 50 mL of EA and was washed with 3×20 mL of brine. The combined organic layers were dried over anhydrous sodium sulfate and concentrated under vacuum. The residue was applied onto a silica gel column with ethyl acetate/petroleum ether (2:1) as eluent to get 300 mg (crude) product. The crude product (300 mg) was purified by Prep-HPLC with the following conditions (Prep-HPLC-020): Column, XSelect CSH Prep C18 OBD Column, 19*150 mm 5 um 13 nm; mobile phase, Water with 10 mmol $NH_4HCO_3$ and ACN (20.0% ACN up to 61.0% in 8 min); Detector. Waters 2489 254&220 nm. This resulted in 130 mg (16%) of methyl 5-[1-(2-hydroxyethyl)-4-methyl-5-oxo-2,5-dihydro-1H-pyrazol-3-yl]-2,4-dimethylbenzoate as a white solid.

Step 4.

To a solution of methyl 5-[1-(2-hydroxyethyl)-4-methyl-5-oxo-2,5-dihydro-1H-pyrazol-3-yl]-2,4-dimethylbenzoate (120 mg, 0.39 mmol, 1.00 equiv) in methanol (6 mL) was added a solution of sodium hydroxide (47 mg, 1.18 mmol, 3.00 equiv) in water (3 mL). The resulting solution was stirred for 4 h at 50° C., then was concentrated under vacuum. The pH value of the solution was adjusted to 3-4 with hydrogen chloride (6 mol/L). The resulting solution was extracted with 20 mL of ethyl acetate and the combined organic layers was washed with 1×10 mL of brine, dried over anhydrous sodium sulfate and concentrated under vacuum. This resulted in 100 mg (87%) of 5-[1-(2-hydroxyethyl)-4-methyl-5-oxo-2,5-dihydro-1H-pyrazol-3-yl]-2,4-dimethylbenzoic acid as a white solid.

Step 5.

Into a 100-mL round-bottom flask, was placed 5-[1-(2-hydroxyethyl)-4-methyl-5-oxo-2,5-dihydro-1H-pyrazol-3-yl]-2,4-dimethylbenzoic acid (114 mg, 0.39 mmol, 1.00 equiv) in dichloromethane (10 mL). Then EDCI (149 mg, 1.01 mmol, 2.00 equiv), 4-dimethylaminopyridine (96 mg, 0.79 mmol, 2.00 equiv), DIEA (152 mg, 1.18 mmol, 3.00 equiv) and 4-(azetidin-3-yl)benzonitrile hydrochloride (92 mg, 0.47 mmol, 1.20 equiv) were added to the reaction. The resulting solution was stirred for 1 overnight at room temperature. The resulting solution was diluted with 20 mL of ethyl acetate. The resulting mixture was washed with 2×10 mL of Brine. The mixture was dried over anhydrous sodium sulfate and concentrated under vacuum. The residue was applied onto a silica gel column with dichloromethane/methanol (20:1). This resulted in 100 mg (59%) of 4-[1-([5-[1-(2-hydroxyethyl)-4-methyl-5-oxo-2,5-dihydro-1H-pyrazol-3-yl]-2,4-dimethylphenyl]carbonyl)azetidin-3-yl] benzonitrile (Compound 5) as a white solid. LC-MS: (ES, m/z): [M+H]$^+$ 431. H-NMR: (300 MHz, CD3OD, ppm): 7.768-7.740 (2H, d, J=8.4 Hz), 7.591-7.563 (2H, d, J=8.4 Hz), 7.295-7.225 (2H, d, J=21), 4.664-4.603 (1H, m), 4.499-4.424 (1H, m), 4.283-4.196 (3H, m), 4.112-4.011 (2H, m), 3.911-3.879 (2H, t), 2.438 (3H, s), 2.239 (3H, s), 1.825 (3H, s).

Synthesis of Compound 6

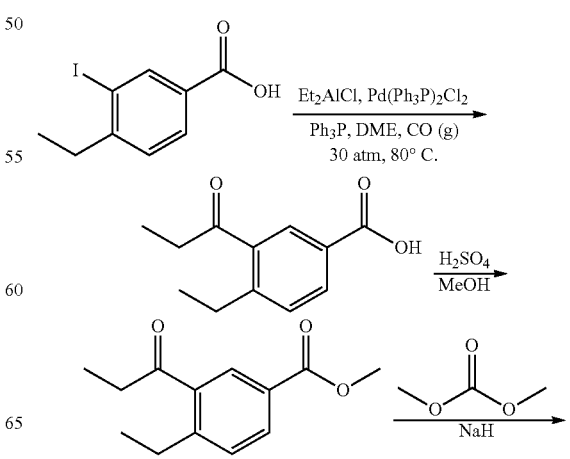

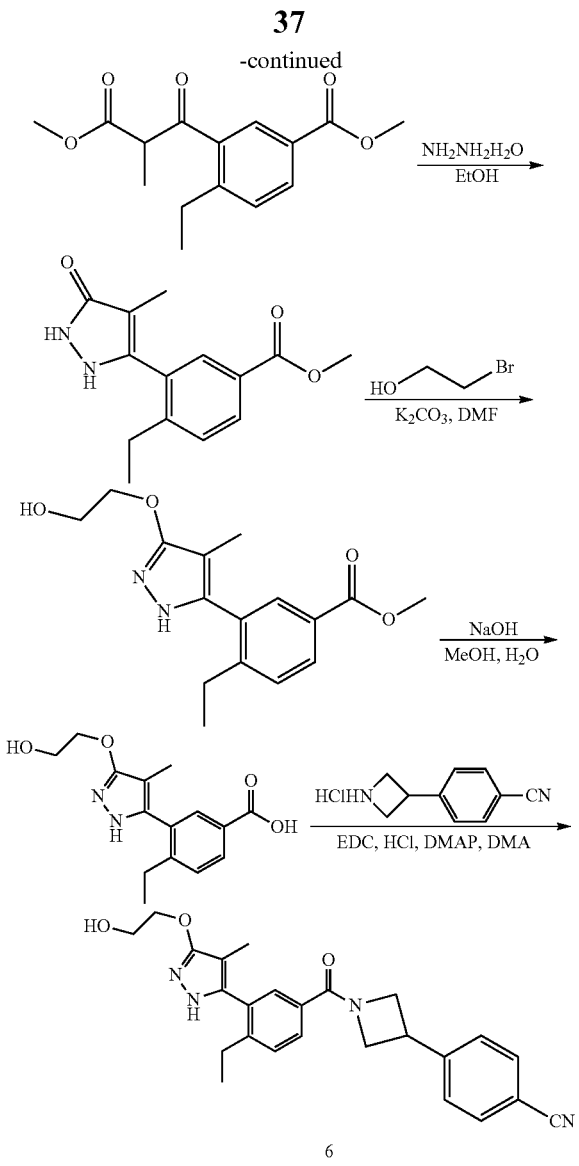

Step 1.

Into a 250-mL round-bottom flask purged and maintained with an inert atmosphere of nitrogen, was placed 4-ethyl-3-iodobenzoic acid (10 g, 36.22 mmol, 1.00 equiv), ethylene glycol dimethyl ether (130 mL), PPh$_3$ (1.97 g, 7.51 mmol, 0.20 equiv), Pd(PPh3)$_2$Cl$_2$ (5.29 g, 7.54 mmol, 0.20 equiv). This was followed by the addition of Et$_2$AlCl (2 mol/L in toluene) (56.5 mL, 113 mmol, 3.00 equiv) dropwise at 0° C. The temperature was increased to room temperature gradually. Then the solution was transferred to a 250-mL pressure tank reactor. To the above CO(g) (40 atm) was introduced in. The resulting solution was stirred for 1 overnight at 80° C. under an atmosphere of carbon monoxide. The reaction was then quenched with 150 mL of water. The solids were removed by filtration and the filtrate was concentrated under vacuum. The pH value of the solution was adjusted to 2-3 with hydrogen chloride (2 mol/L). The aqueous phase was extracted with 3×60 mL of ethyl acetate and the combined organic layers were washed with 1×60 mL of brine, dried over anhydrous sodium sulfate and concentrated under vacuum. The residue was applied onto a silica gel column with ethyl acetate/petroleum ether (1:6) as eluent to yield 4.6 g (62%) of 4-ethyl-3-propanoylbenzoic acid as red oil.

Step 2.

To a solution of 4-ethyl-3-propanoylbenzoic acid (7.6 g, 36.85 mmol, 1.00 equiv) in methanol (80 mL) was added sulfuric acid (7.23 g, 73.72 mmol, 2.00 equiv) dropwise with stirring at room temperature. The resulting solution was stirred for 1 overnight at 80° C. in, then concentrated under vacuum. The reaction was quenched with 100 mL of water/ice. The aqueous phase extracted with 3×30 mL of ethyl acetate and the combined organic layers were washed with 1×30 mL of sodium bicarbonate (sat.) and 1×30 mL of brine, dried over anhydrous sodium sulfate and concentrated under vacuum. The residue was applied onto a silica gel column with ethyl acetate/petroleum ether (1:250) as eluent to furnish 6.17 g (76%) of methyl 4-ethyl-3-propanoylbenzoate as brown oil.

Step 3.

To a solution of methyl 4-ethyl-3-propanoylbenzoate (6.12 g, 27.78 mmol, 1.00 equiv) in dimethyl carbonate (70 mL) was added sodium hydride (4.49 g, 112.25 mmol, 4.00 equiv, 60%) in portions at 0° C. The resulting solution was stirred for 1 h at 80° C., then quenched with 70 mL of water/ice. The aqueous phase was extracted with 2×50 mL of ethyl acetate and the combined organic layers were washed with 1×30 mL of brine, dried over anhydrous sodium sulfate and concentrated under vacuum. The residue was applied onto a silica gel column with ethyl acetate/petroleum ether (1:25) as eluent to afford 3.4 g (44%) of methyl 4-ethyl-3-(3-methoxy-2-methyl-3-oxopropanoyl) benzoate as yellow oil.

Step 4.

To a solution of methyl 4-ethyl-3-(3-methoxy-2-methyl-3-oxopropanoyl)benzoate (700 mg, 2.52 mmol, 1.00 equiv) in ethanol (8 mL) was added NH$_2$NH$_2$.H$_2$O (504 mg, 10.08 mmol, 4.00 equiv). The resulting solution was stirred for 3 h at 80° C., then concentrated under vacuum. The residue was applied onto a silica gel column with ethyl acetate/petroleum ether (4:1) as eluent to yield 314 mg (48%) of methyl 4-ethyl-3-(4-methyl-5-oxo-2,5-dihydro-1H-pyrazol-3-yl)benzoate as a yellow solid.

Step 5.

To a solution of methyl 4-ethyl-3-(4-methyl-5-oxo-2,5-dihydro-1H-pyrazol-3-yl)benzoate (314 mg, 1.21 mmol, 1.00 equiv) in N,N-dimethylformamide (5 g, 68.41 mmol, 56.71 equiv) was added potassium carbonate (217 mg, 1.57 mmol, 1.30 equiv) and 2-bromoethan-1-ol (225 mg, 1.80 mmol, 1.50 equiv). The resulting solution was stirred for 1 overnight at room temperature, then diluted with 30 mL of ethyl acetate. The organic layer was washed with 1×10 mL of water and 2×10 mL of brine, dried over anhydrous sodium sulfate and concentrated under vacuum. The residue was applied onto a silica gel column with ethyl acetate/petroleum ether (7:5) as eluent. The crude product was purified by Prep-HPLC with the following conditions (Prep-HPLC-020): Column, Sunfire Prep C18 OBD Column, 19*150 mm 5 um 10 nm; mobile phase, Water with 10 mmol NH$_4$HCO$_3$ and ACN (20.0% ACN up to 63.0% in 8 min); Detector, Waters 2489 254&220 nm. This resulted in 40 mg (10%) of methyl 4-ethyl-3-[1-(2-hydroxyethoxy)-4-methyl-5-oxo-2, 5-dihydro-1H-pyrazol-3-yl]benzoate as a white solid.

Step 6.

To a solution of methyl 4-ethyl-3-[3-(2-hydroxyethoxy)-4-methyl-1H-pyrazol-5-yl]benzoate (70 mg, 0.23 mmol, 1.00 equiv) in methanol (1 mL) was added a solution of sodium hydroxide (37 mg, 0.93 mmol, 4.00 equiv) in water (0.5 mL). The resulting solution was stirred for 1 h at 70° C., then concentrated under vacuum. The pH value of the solution was adjusted to 2 with hydrogen chloride (2 mol/L).

The resulting mixture was concentrated under vacuum. This resulted in 120 mg (crude) of 4-ethyl-3-[1-(2-hydroxy-ethoxy)-4-methyl-5-oxo-2,5-dihydro-1H-pyrazol-3-yl]benzoic acid as a yellow solid.

Step 7.

Into a 25-mL round-bottom flask, was placed 4-ethyl-3-[3-(2-hydroxyethoxy)-4-methyl-1H-pyrazol-5-yl]benzoic acid (170 mg, 0.59 mmol, 1.00 equiv) in DMA (3 mL). EDC.HCl (225 mg, 1.17 mmol, 2.00 equiv), 4-dimethylaminopyridine (143 mg, 1.17 mmol, 2.00 equiv) and 4-(azetidin-3-yl)benzonitrile hydrochloride (227 mg, 1.17 mmol, 2.00 equiv) were added to the reaction. The resulting solution was stirred for 1 overnight at room temperature, then diluted with 10 mL of ethyl acetate. The organic layer was washed with 2×10 mL of water and 1×10 mL of brine, dried over anhydrous sodium sulfate and concentrated under vacuum. The crude product was purified by Prep-HPLC with the following conditions (Prep-HPLC-020): Column. XBridge Prep Shield RP18 OBD Column, 19*150 mm Sum 13 nm; mobile phase, Water with 10 mmol $NH_4HCO_3$ and ACN (20.0% ACN up to 52.0% in 8 min); Detector, Waters 2489 254&220 nm. This resulted in 45.1 mg (18%) of 4-[1-([4-ethyl-3-[3-(2-hydroxyethoxy)-4-methyl-1H-pyrazol-5-yl]phenyl]carbonyl)azetidin-3-yl]benzonitrile (Compound 6) as a white solid. LC-MS: (ES, m/z): [M+H]+ 431. H-NMR: (300 MHz, $CD_3OD$, ppm): δ 7.762-7.720 (3H, m), 7.608-7.485 (4H, m), 4.96-4.91 (1H, m), 4.665-4.605 (1H, t), 4.459 (1H, m), 4.287-4.193 (3H, m), 4.138-4.057 (1H, m), 3.909-3.877 (2H, t), 2.673-2.597 (2H, m), 1.815 (3H, s), 1.122-1.071 (3H, t).

Synthesis of Compound 7

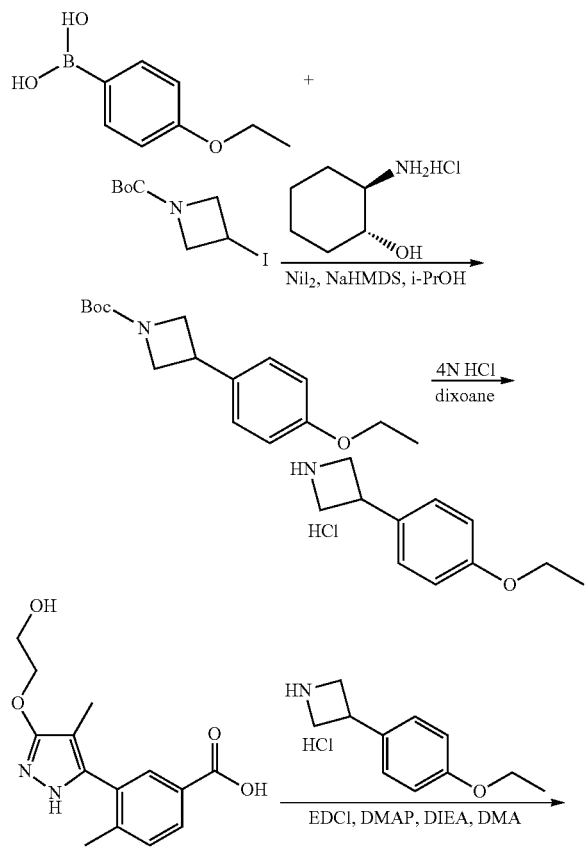

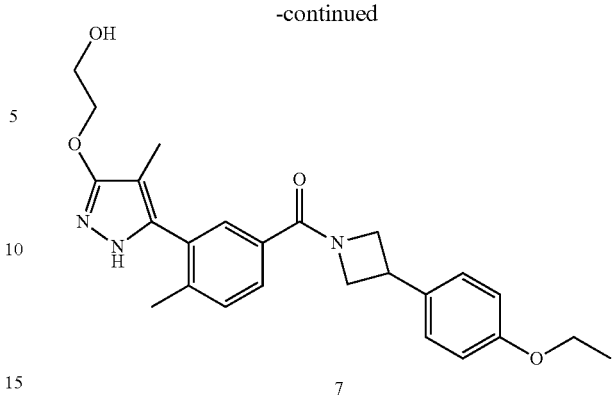

7

Step 1.

To a solution of (4-ethoxyphenyl)boronic acid (150 g, 903.71 mmol, 2.00 equiv) in i-propanol (1.5 L) was added $NiI_2$ (14.1 g, 45.19 mmol, 0.10 equiv), (1R,2R)-2-aminocyclohexan-1-ol hydrochloride (6.82 g, 44.98 mmol, 0.10 equiv), and NaHMDS (2M in THF) (451.8 mL, 902.00 mmol, 2.00 equiv) dropwise, then added tert-butyl 3-iodo-azetidine-1-carboxylate (127.9 g, 451.77 mmol, 1.00 equiv). The resulting solution was stirred for 3 h at 80° C. under nitrogen and concentrated under vacuum, then diluted with 1 L of water. The aqueous phase was extracted with 2×1000 mL of ethyl acetate and the combined organic layers were washed with 2×500 mL of brine, dried over anhydrous sodium sulfate and concentrated under vacuum. The residue was applied onto a silica gel column with ethyl acetate/petroleum ether (1:20) as eluent to furnish 48 g (38%) of tert-butyl 3-(4-ethoxyphenyl)azetidine-1-carboxylate as yellow oil.

Step 2.

To a solution of tert-butyl 3-(4-ethoxyphenyl)azetidine-1-carboxylate (48 g, 173.06 mmol, 1.00 equiv) in dioxane (300 mL) was added 4N hydrogen chloride (150 mL). The resulting solution was stirred for 2 h at 60° C., then concentrated under vacuum. The residue was washed with 1×500 mL of EtOAc/ACN (10:1) to afford 30 g (81%) of 3-(4-ethoxyphenyl)azetidine hydrochloride as a white solid.

Step 3.

To a solution of 3-(3-(2-hydroxyethoxy)-4-methyl-1H-pyrazol-5-yl)-4-methylbenzoic acid (300 mg, 1.09 mmol, 1.00 equiv) in DMA (10 mL) was added EDCI (417 mg, 2.18 mmol, 2.00 equiv), DIEA (420 mg, 3.25 mmol, 3.00 equiv), 4-dimethylaminopyridine (26 mg, 0.21 mmol, 0.20 equiv) and 3-(4-ethoxyphenyl)azetidine hydrochloride (278 mg, 1.30 mmol, 1.20 equiv). The resulting solution was stirred for 1.5 h at 40° C., then quenched with 20 mL of NH4Cl (sat.). The aqueous phase was extracted with 3×30 mL of ethyl acetate and the combined organic layers were dried over anhydrous sodium sulfate and concentrated under vacuum. The crude product (200 mg) was purified by Prep-HPLC with the following conditions (Prep-HPLC-020): Column, Xbridge Prep Shield RP18 OBD Column, 19*150 mm 5 um 13 nm; mobile phase, water with 0.05% TFA and MeCN (33.0% MeCN up to 46.0% in 8 min); Detector, Waters 2489 254&220 nm. This resulted in 68.6 mg (15%) of (3-(4-ethoxyphenyl)azetidin-1-yl)(3-(3-(2-hydroxyethoxy)-4-methyl-1H-pyrazol-5-yl)-4-methylphenyl)methanone (Compound 7) as a white solid. LC-MS: (ES, m/z): [M+H]436. H-NMR: (300 Hz, $CD_3OD$, ppm): δ 7.69 (1H, m), 7.56 (1H, d, J=8.4 Hz), 7.44 (1H, d, 8.7 Hz), 7.31 (2H, m), 6.92 (2H, m), 4.87 (1H, m), 4.77 (1H, m), 4.37 (1H, m), 4.27 (2H, m), 4.17 (1H, m), 4.02 (2H, m), 3.55 (3H, m), 2.30 (3H, s), 1.84 (3H, s), 1.38 (3H, t).

Synthesis of Compound 8

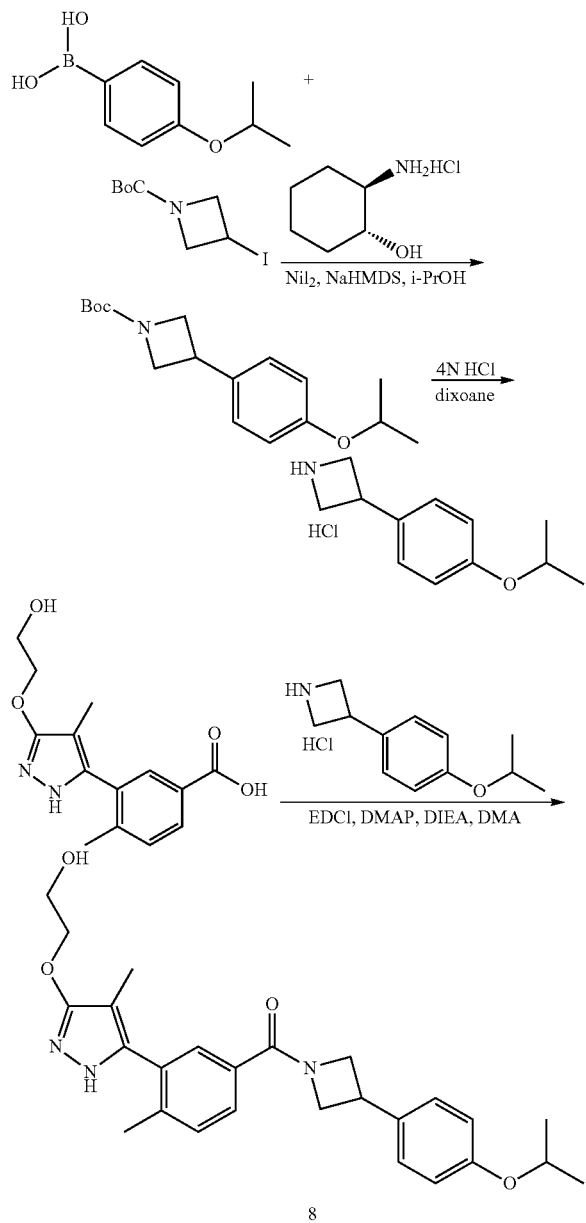

Step 1.

To a solution of [4-(propan-2-yloxy)phenyl]boronic acid (9.0 g, 50.00 mmol, 2.00 equiv) in i-propanol (150 mL) was added $NiI_2$ (1.6 g, 5.13 mmol, 0.20 equiv), (1R,2R)-2-aminocyclohexan-1-ol hydrochloride (760 mg, 5.01 mmol, 0.20 equiv) and NaHMDS (2M in THF) (25 mL, 50.00 mmol, 2.00 equiv) dropwise, then added tert-butyl 3-iodo-azetidine-1-carboxylate (7.1 g, 25.08 mmol, 1.00 equiv). The resulting solution was stirred for 2 h at 80° C. under nitrogen, and concentrated under vacuum, then diluted with 100 mL of water. The aqueous phase was extracted with 2×100 mL of ethyl acetate and the combined organic layers were washed with 2×50 mL of brine, dried over anhydrous sodium sulfate and concentrated under vacuum. The residue was applied onto a silica gel column with ethyl acetate/petroleum ether (1:20) as eluent to yield 2 g (27%) of tert-butyl 3-[4-(propan-2-yloxy)phenyl]azetidine-1-carboxylate as a yellow solid.

Step 2.

To a solution of tert-butyl 3-[4-(propan-2-yloxy)phenyl]azetidine-1-carboxylate (250 mg, 0.86 mmol, 1.00 equiv) in dioxane (10 mL) was added 4N hydrogen chloride (5 mL). The resulting solution was stirred for 2 h at 60° C., then concentrated under vacuum. The residue was washed with 1×50 mL of EtOAc to afford to 150 mg (77%) of 3-[4-(propan-2-yloxy)phenyl]azetidine hydrochloride as a white solid.

Step 3.

To a solution of 3-[3-(2-hydroxyethoxy)-4-methyl-1H-pyrazol-5-yl]-4-methylbenzoic acid (300 mg, 1.09 mmol, 1.00 equiv) in DMA (10 mL) was added EDCI (417 mg, 2.18 mmol, 2.00 equiv), DIEA (420 mg, 3.25 mmol, 3.00 equiv), 4-dimethylaminopyridine (25 mg, 0.20 mmol, 0.20 equiv) and 3-[4-(propan-2-yloxy)phenyl]azetidine hydrochloride (275 mg, 1.21 mmol, 1.20 equiv). The resulting solution was stirred for overnight at 25° C., then quenched with 30 mL of NH4Cl (sat.). The aqueous phase was extracted with 3×30 mL of ethyl acetate and the combined organic layers were dried over anhydrous sodium sulfate. The crude product (200 mg) was purified by Prep-HPLC with the following conditions (Prep-HPLC-020): Column, XBridge Prep Shield RP18 OBD Column, 19*150 mm Sum 13 nm; mobile phase. Water with 10 mmol $NH_4HCO_3$ and MeCN (37.0% MeCN up to 52.0% in 8 min); Detector, Waters 2489 254&220 nm. This resulted in 104.8 mg (21%) of 2-([4-methyl-5-[2-methyl-5-([3-[4-(propan-2-yloxy)phenyl]azetidin-1-yl]carbonyl)phenyl]-1H-pyrazol-3-yl]oxy)ethan-1-ol (Compound 8) as a white solid. LC-MS: (ES, m/z): [M+H]$^+$ 450. H-NMR: (300 Hz, $CD_3OD$, ppm): δ 7.67 (1H, m), 7.56 (1H, d, J=8.4 Hz), 7.46 (1H, d, 8.1 Hz), 7.29 (2H, m), 6.91 (2H, m), 4.76 (1H, m), 4.64 (2H, m), 4.36 (1H, m), 4.27 (2H, m), 4.17 (1H, m), 3.96 (3H, m), 2.29 (3H, s), 1.84 (3H, s), 1.31 (6H, d).

Synthesis of Compound 9

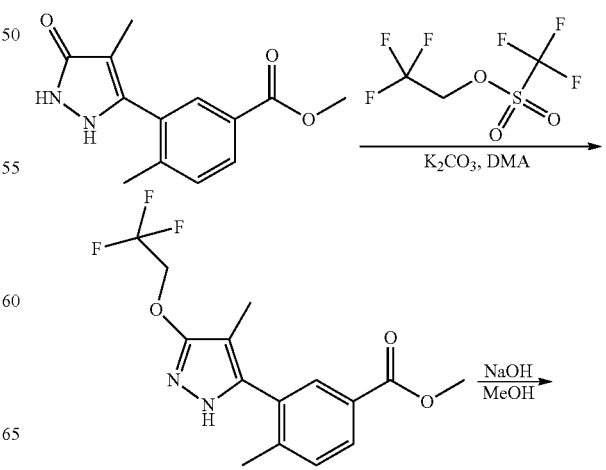

-continued

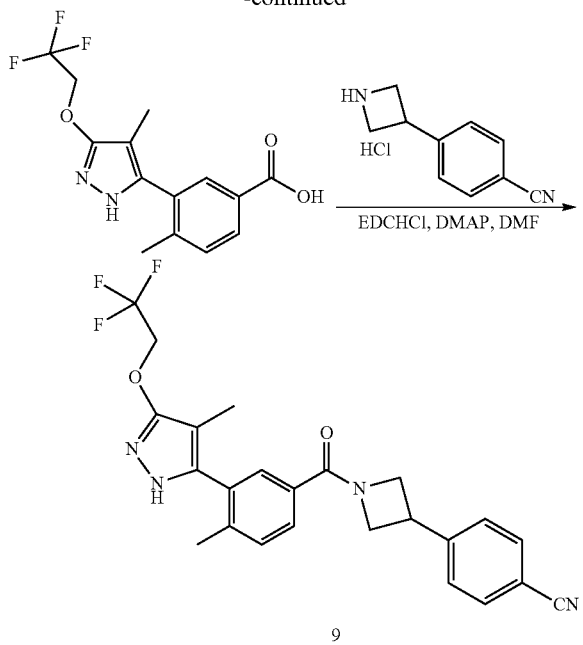

Step 1.

To a solution of methyl 4-methyl-3-(4-methyl-5-oxo-2,5-dihydro-1H-pyrazol-3-yl)benzoate (500 mg, 2.03 mmol, 1.00 equiv) in DMA (10 mL) was added potassium carbonate (1.4 g, 10.13 mmol, 5.00 equiv), 2,2,2-trifluoroethyl trifluoromethanesulfonate (1.4 g, 6.03 mmol, 3.00 equiv). The resulting solution was stirred for 3 h at 25° C., then diluted with 30 mL of H$_2$O. The aqueous phase was extracted with 4×30 mL of ethyl acetate and the combined organic layers were washed with 1×50 mL of brine, dried over anhydrous sodium sulfate. The residue was applied onto a silica gel column with ethyl acetate/petroleum ether (1:15) as eluent to furnish 380 mg (57%) of methyl 4-methyl-3-[4-methyl-3-(2,2,2-trifluoroethoxy)-1H-pyrazol-5-yl]benzoate as a white solid.

Step 2.

To a solution of methyl 4-methyl-3-[4-methyl-3-(2,2,2-trifluoroethoxy)-1H-pyrazol-5-yl]benzoate (300 mg, 0.91 mmol, 1.00 equiv) in MeOH (10 mL) was added a solution of sodium hydroxide (183 mg, 4.58 mmol, 5.00 equiv) in H$_2$O (5 mL). The resulting solution was stirred for overnight at 25° C., then concentrated under vacuum. The pH value of the solution was adjusted to 5 with hydrogen chloride (2 mol/L). The solids were collected by filtration. This resulted in 240 mg (84%) of 4-methyl-3-[4-methyl-3-(2,2,2-trifluoroethoxy)-1H-pyrazol-5-yl]benzoic acid as a white solid.

Step 3.

To a solution of 4-methyl-3-[4-methyl-3-(2,2,2-trifluoroethoxy)-1H-pyrazol-5-yl]benzoic acid (250 mg, 0.80 mmol, 1.00 equiv) in DMA (10 mL) was added EDCI (305 mg, 1.59 mmol, 2.00 equiv), 4-dimethylaminopyridine (15 mg, 0.12 mmol, 0.15 equiv), DIEA (308 mg, 2.38 mmol, 3.00 equiv) and 4-(azetidin-3-yl)benzonitrile hydrochloride (185 mg, 0.95 mmol, 1.20 equiv). The resulting solution was stirred for 2.5 h at 25° C., then quenched with 20 mL of NH$_4$Cl (sat). The aqueous phase was extracted with 4×20 mL of ethyl acetate and the combined organic layers were washed with 1×20 mL of brine, dried over anhydrous sodium sulfate. The crude product (300 mg) was purified by Prep-HPLC with the following conditions (Prep-HPLC-020): Column, XBridge Prep BEH130 C18 Column, 19*100 mm 5 um 13 nm; mobile phase, Water with 10 mmol NH$_4$HCO$_3$ and MeCN (45.0% MeCN up to 70.0% in 8 min); Detector, Waters 2489 254&220 nm. This resulted in 195.4 mg (54%) of 4-[1-([4-methyl-3-[4-methyl-3-(2,2,2-trifluoroethoxy)-1H-pyrazol-5-yl]phenyl]carbonyl)azetidin-3-yl]benzonitrile (Compound 9) as a white solid. LC-MS: (ES, m/z): [M+H]$^+$ 455. H-NMR: (300 Hz, CD$_3$OD, ppm): δ 7.69 (3H, m), 7.56 (3H, d, J=8.1 Hz), 7.43 (1H, d, 8.1 Hz), 4.75 (4H, m), 4.18 (1H, m), 4.15 (2H, m), 2.25 (3H, m), 1.80 (3H, m).

Synthesis of Compound 10

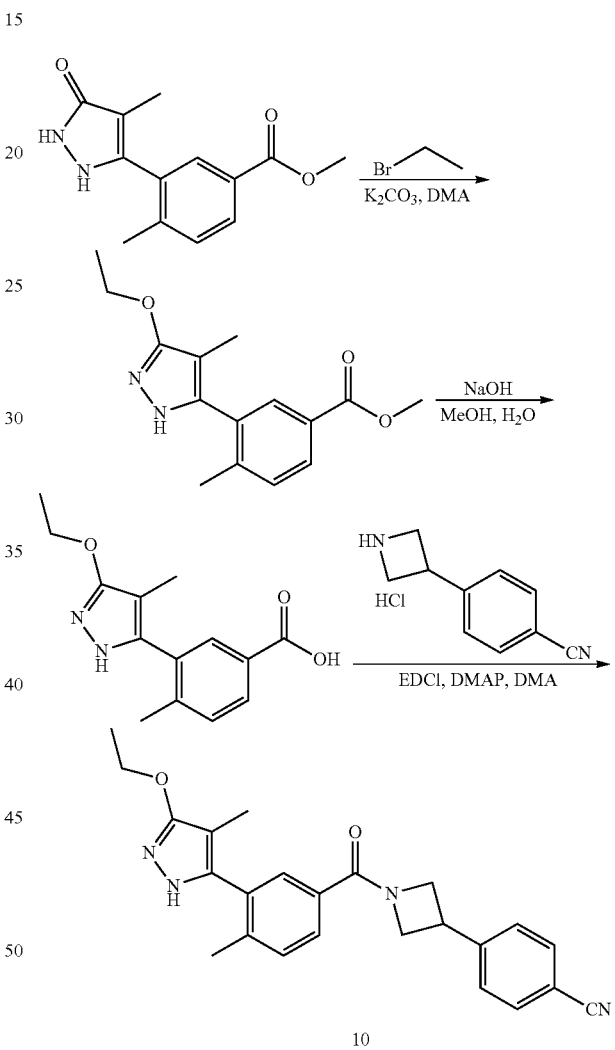

Step 1.

To a solution of methyl 4-methyl-3-(4-methyl-5-oxo-2,5-dihydro-1H-pyrazol-3-yl)benzoate (500 mg, 2.03 mmol, 1.00 equiv) in DMA (10 mL) was added potassium carbonate (1.4 g, 10.13 mmol, 5.00 equiv) and bromoethane (2.0 g, 18.35 mmol, 7.00 equiv). The resulting solution was stirred for 5 h at 25° C., then quenched with 20 mL of water. The aqueous phase was extracted with 5×50 mL of ethyl acetate and the combined organic layers were washed with 2×100 mL of brine, dried over anhydrous sodium sulfate and concentrated under vacuum. The residue was applied onto a silica gel column with ethyl acetate/petroleum ether (1:20 to 1:2) as eluent to yield 150 mg (27%) of methyl 3-(3-ethoxy-4-methyl-1H-pyrazol-5-yl)-4-methylbenzoate as yellow oil.
Step 2.

To a solution of methyl 3-(3-ethoxy-4-methyl-1H-pyrazol-5-yl)-4-methylbenzoate (150 mg, 0.55 mmol, 1.00 equiv) in methanol (10 mL) was added a solution of sodium hydroxide (219 mg, 5.47 mmol, 10.00 equiv) in water (5 mL). The resulting solution was stirred overnight at 25° C., then concentrated under vacuum. The pH value of the solution was adjusted to 5 with hydrogen chloride (2 mol/L). The solids were collected by filtration. This resulted in 90 mg (63%) of 3-(3-ethoxy-4-methyl-1H-pyrazol-5-yl)-4-methylbenzoic acid as a white solid.
Step 3.

To a solution of 3-(3-ethoxy-4-methyl-1H-pyrazol-5-yl)-4-methylbenzoic acid (90 mg, 0.35 mmol, 1.00 equiv) in DMA (10 mL) was added EDCI (133 mg, 0.69 mmol, 2.00 equiv), 4-dimethylaminopyridine (84.5 mg, 0.69 mmol, 2.00 equiv), and 4-(azetidin-3-yl)benzonitrile hydrochloride (80.6 mg, 0.41 mmol, 1.20 equiv). The resulting solution was stirred for 6 h at 25° C., then quenched with 20 mL of water. The aqueous phase was extracted with 3×50 mL of ethyl acetate and the combined organic layers were washed with 1×30 mL of NH4Cl (sat) and 2×50 mL of brine, dried over anhydrous sodium sulfate and concentrated under vacuum. The crude product (100 mg) was purified by Prep-HPLC with the following conditions (Prep-HPLC-006): Column, XBridge Prep C18 OBD Column, 19*150 mm 5 um 13 nm; mobile phase, Water with 10 mmol NH4HCO3 and ACN (39.0% ACN up to 57.0% in 8 min); Detector, Waters 2489 254&220 nm. This resulted in 81.5 mg (59%) of 4-(1-[[3-(3-ethoxy-4-methyl-1H-pyrazol-5-yl)-4-methylphenyl]carbonyl]azetidin-3-yl)benzonitrile (Compound 10) as a white solid. LC-MS: (ES, m/z): [M+H]+ 401. H-NMR: (300 MHz, CD3OD, ppm): δ 7.79 (2H, m), 7.71 (1H, m), 7.60 (3H, in), 7.46 (1H, d, J=8.1), 4.82 (1H, in), 4.65 (1H, in), 4.46 (1H, m), 4.25 (3H, m), 4.10 (1H, m), 2.30 (3H, s), 2.00 (3H, s), 1.40 (3H, m).

Synthesis of Compound 11

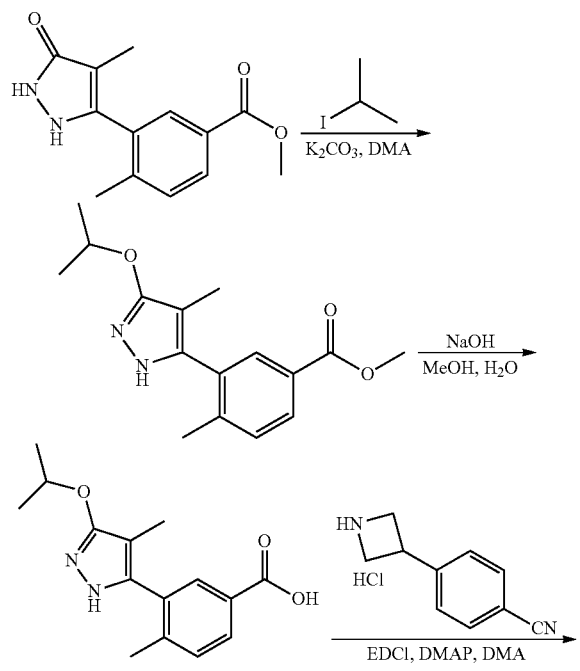

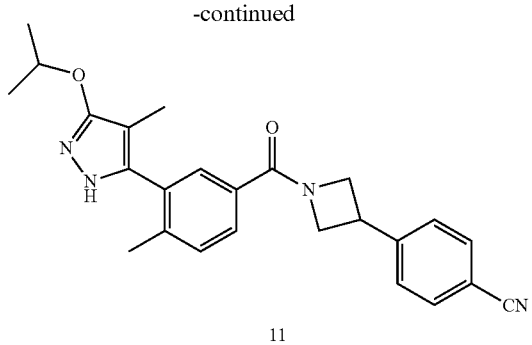

11

Step 1.

To a solution of methyl 4-methyl-3-(4-methyl-5-oxo-2,5-dihydro-1H-pyrazol-3-yl)benzoate (500 mg, 2.03 mmol, 1.00 equiv) in DMA (10 mL) was added K2CO3 (1.4 g, 10.06 mmol, 5.00 equiv) and 2-iodopropane (2.4 g, 14.12 mmol, 7.00 equiv). The resulting solution was stirred for 3 h at 25° C., then quenched with 20 mL of water. The aqueous phase was extracted with 5×50 mL of ethyl acetate and the combined organic layers were washed with 2×100 mL of brine, dried over anhydrous sodium sulfate and concentrated under vacuum. The residue was applied onto a silica gel column with ethyl acetate/petroleum ether (1:10 to 1:2) as eluent to yield 500 mg (85%) of methyl 4-methyl-3-[4-methyl-3-(propan-2-yloxy)-1H-pyrazol-5-yl]benzoate as yellow oil.
Step 2.

To a solution of methyl 4-methyl-3-[4-methyl-3-(propan-2-yloxy)-1H-pyrazol-5-yl]benzoate (300 mg, 1.04 mmol, 1.00 equiv) in methanol (10 mL) was added a solution of sodium hydroxide (417 mg, 10.43 mmol, 10.00 equiv) in water (5 mL). The resulting solution was stirred overnight at 25° C., then concentrated under vacuum. The pH value of the solution was adjusted to 5 with hydrogen chloride (2 mol/L). The solids were collected by filtration. This resulted in 200 mg (70%) of 4-methyl-3-[4-methyl-3-(propan-2-yloxy)-1H-pyrazol-5-yl]benzoic acid as a white solid.
Step 3.

To a solution of 4-methyl-3-[4-methyl-3-(propan-2-yloxy)-1H-pyrazol-5-yl]benzoic acid (200 mg, 0.73 mmol, 1.00 equiv) in DMA (10 mL) was added EDCI (280.3 mg, 1.46 mmol, 2.00 equiv), 4-dimethylaminopyridine (178.1 mg, 1.46 mmol, 2.00 equiv) and 4-(azetidin-3-yl)benzonitrile hydrochloride (170 mg, 0.87 mmol, 1.20 equiv). The resulting solution was stirred for 4 h at 25° C., then quenched with 30 mL of water. The aqueous phase was extracted with 3×50 mL of ethyl acetate and the combined organic layers were washed with 1×100 mL of NH4Cl (sat) and 2×50 mL of brine, dried over anhydrous sodium sulfate and concentrated under vacuum. The crude product (200 mg) was purified by Prep-HPLC with the following conditions (Prep-HPLC-006): Column, XBridge Prep C18 OBD Column, 19*150 mm 5 um 13 nm; mobile phase, Water with 10 mmol NH4HCO3 and ACN (43.0% ACN up to 59.0% in 8 min); Detector, Waters 2489 254&220 nm. This resulted in 147.2 mg (49%) of 4-[1-([4-methyl-3-[4-methyl-3-(propan-2-yloxy)-1H-pyrazol-5-yl]phenyl]carbonyl)azetidin-3-yl]benzonitrile (Compound 11) as a white solid. LC-MS: (ES, m/z): [M+H]+ 415. H-NMR: (300 MHz, CD3OD, ppm): δ 7.80 (2H, m), 7.70 (1H, m), 7.60 (3H, m), 7.45 (1H, d, J=7.8), 4.82 (1H, m), 4.65 (1H, m), 4.45 (1H, m), 4.22 (1H, m), 4.15 (1H, m) 2.30 (3H, s), 1.80 (3H, s), 1.35 (6H, m).

Additional Representative Compounds

The following representative compounds in TABLE 1 are synthesized according to (i) the foregoing procedures by selecting appropriate starting materials and (ii) known organic synthesis techniques.

TABLE 1

| Cpd | Structure |
|---|---|
| 12 | 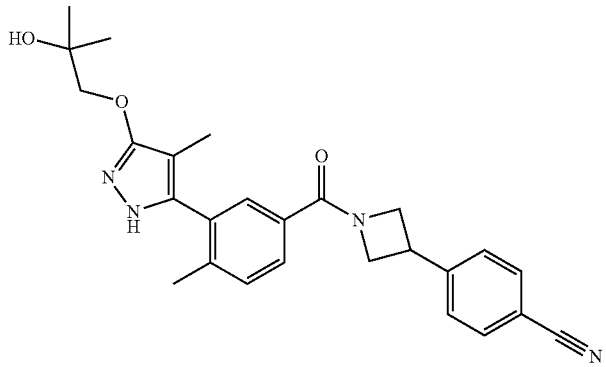 [SMILES: Cc1ccc(C(=O)N2CC(c3ccc(C#N)cc3)C2)cc1-c1[nH]nc(OCC(C)(C)O)c1C] |
| 13 | 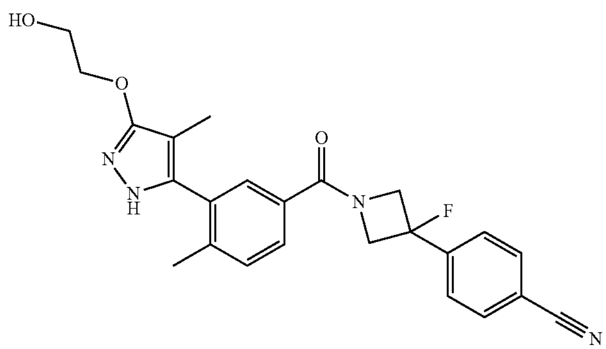 [SMILES: Cc1ccc(C(=O)N2CC(F)(c3ccc(C#N)cc3)C2)cc1-c1[nH]nc(OCCO)c1C] |
| 14 | 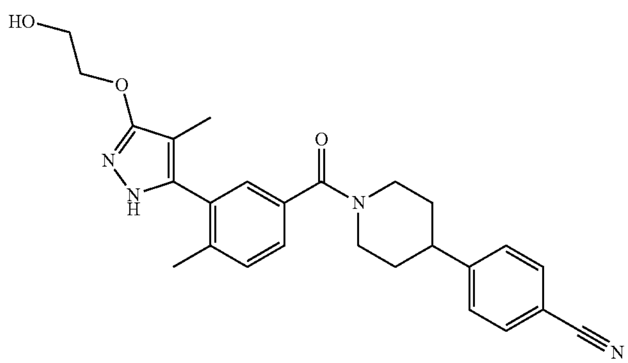 [SMILES: Cc1ccc(C(=O)N2CCC(c3ccc(C#N)cc3)CC2)cc1-c1[nH]nc(OCCO)c1C] |
| 15 | 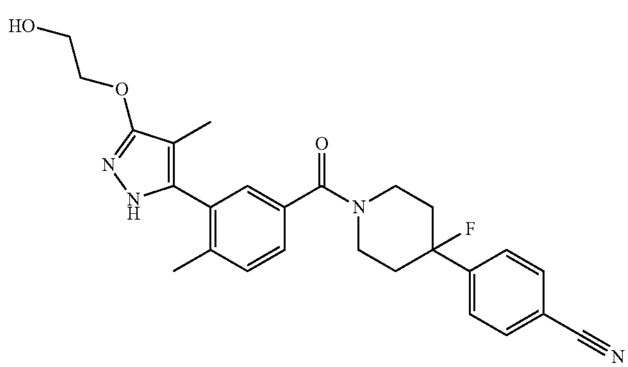 [SMILES: Cc1ccc(C(=O)N2CCC(F)(c3ccc(C#N)cc3)CC2)cc1-c1[nH]nc(OCCO)c1C] |

TABLE 1-continued
| Cpd | Structure |
|---|---|
| 16 | 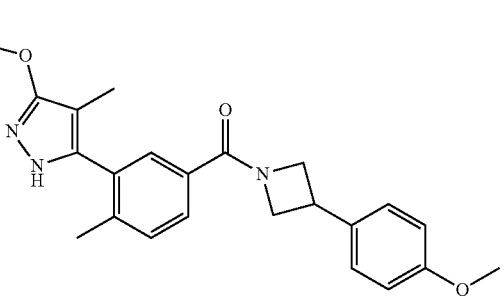 |
| 17 | 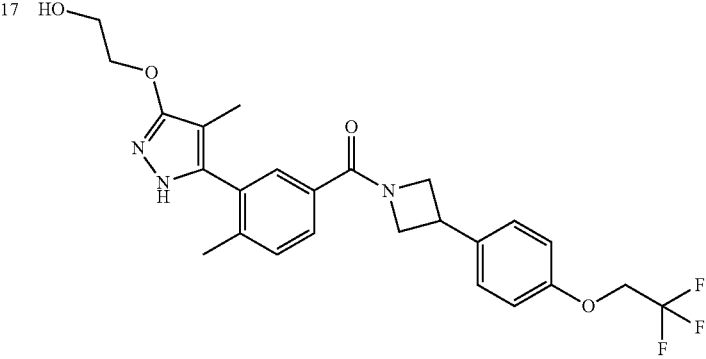 |
| 18 | 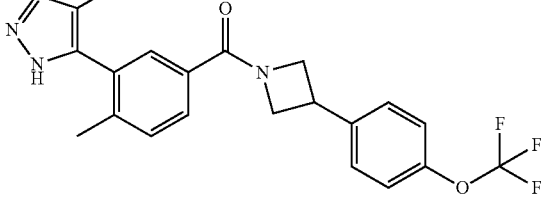 |
| 19 | 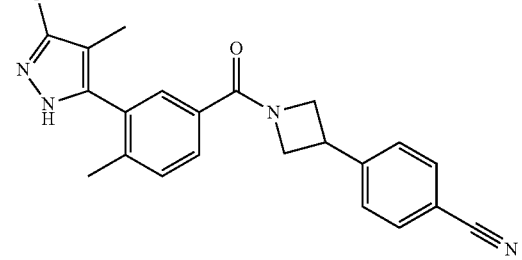 |

TABLE 1-continued

| Cpd | Structure |
|---|---|
| 20 | 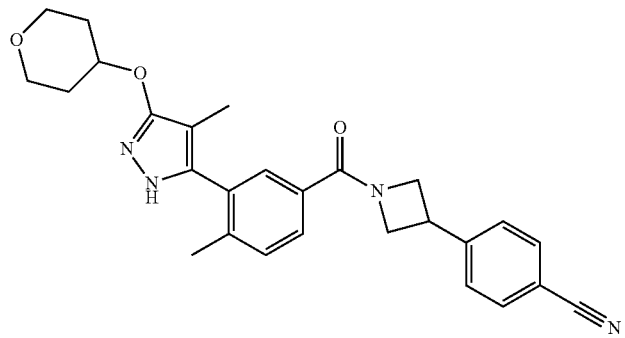 [SMILES: Cc1ccc(C(=O)N2CC(c3ccc(C#N)cc3)C2)cc1-c1[nH]nc(OC2CCOCC2)c1C] |

Example 2

Activity of Compound of the Present Disclosure

FASN Inhibition by Compounds of the Present Disclosure

Determination of FASN Biochemical Activity:

The FASN enzyme was isolated from SKBr3 cells. SKBr3 is a human breast cancer cell-line with high levels of FASN expression. It is estimated that FASN comprises about 25% of the cytosolic proteins in this cell line. SKBr3 cells were homogenized in a dounce homogenizer then centrifuged for 15 minutes at 4° C. to remove particulate matter. The supernatant was then analyzed for protein content, diluted to the appropriate concentration, and used to measure FASN activity. The presence of FASN was confirmed by western blot analysis. A similar method for isolation of FASN from SKBr3 cells is described in Teresa, P. et al. (*Clin. Cancer Res.* 2009; 15(24), 7608-7615).

FASN activity of the SKBr3 cell extract was determined by measuring either NADPH oxidation or the amount of thiol-containing coenzyme A (CoA) released during the fatty acid synthase reaction. The dye CPM (7-diethylamino-3-(4'-maleimidyl-phenyl)-4-methylcoumarin) contains a thiol reactive group that increases its fluorescence emission on reaction with the sulfhydryl group of CoA. CoA is a byproduct of the FASN reaction, 8 molecules of CoA are released for every molecule of palmitate produced. Reaction of the CoA thiol group with CPM results in fluorescence emission at 405/530 nM.

The biochemical activities shown in TABLE 2 were determined using the fluorescence measurement of CoA release via a procedure described in Chung C. C. et al. (*Assay and Drug Development Technologies*, 2008, 6(3), 361-374). Briefly, compounds were assayed in duplicate across a range of 10 concentrations using a serial 3-fold dilution scheme. Compounds are diluted in DMSO and the final concentration of DMSO in the FASN assay reaction is 2.5%. For the assay, the enzyme and compound are pre-incubated at room temperature (RT) for 15 minutes with shaking at 510 rpm. Following pre-incubation ther reaction is started with addition of the substrate mix (acetyl CoA, Malonyl CoA, and NADPH). The final concentrations of substrates is 200 µM, 500 µM and 1 nM, respectively. The reaction with substrates proceeds at RT for 15 minutes with shaking, at which time CPM is added to the assay with shaking for 20 minutes at RT. Compound activity is then measured by fluorescence at 405/530 nM.

Determination of Palmitate Synthesis Inhibition:

Cells were seeded into 96-well culture plates at a density of 30,000 cells per well. All incubations were performed at 5% $CO_2$ and 37° C. in a tissue culture incubator. After overnight incubation, media was removed from all wells and replaced with media containing both 1 mM 13C2-acetate and TVB-2640 across a range of concentrations (30 µM, 10 µM, 3 µM, 1 µM, 0.3 µM, 0.1 µM, 0.03 µM, 0.01 µM, 0.003 µM, 0.001 µM, all with 0.5% DMSO). All treatments were performed in duplicate and incubated for 18 hours. After 18 hours incubation, the media containing compound and stable-labeled tracer was removed and the cells washed twice with ice cold DPBS. Following DPBS wash, samples were saponifed with 35 µL of 1N sodium hydroxide for 30 minutes at 37° C. Samples were allowed to cool to room temperature and then acidified with 15 µL of 1N formic acid and 50 µL methanol. The samples were centrifuged at 3000×g at 4° C. for 5 minutes to pellet insoluble material. After centrifugation, 100 µL of heptadecanoic acid, internal standard, in methanol was added to all samples to a final concentration of 1 µM. The plate was centrifuged for an additional 5 minutes at 3000×g at 4° C. Supernatant was transferred into a 96-well plate and subjected to LC-MS analysis Bioanalytical analysis was conducted by using LC-MS. HPLC separation was achieved using an XBridge C8, 2.5µ, 130 Å, 50×2.1 mm column (Waters Corporation, Milford, Mass.). The columns were equilibrated for 1 hour prior to running samples. Both mobile phase A (water) and B (acetonitrile) were HPLC grade. The flow rate was 0.5 mL/min and the column was re-equilibrated at 60% B for 2 minutes prior to the next injection. The mass spectrometer, API4000, was run in SRM mode for analyte detection.

The raw LC-MS peak area ratios (peak area of analyte/peak area of internal standard) were determined using Analyst 1.5 software (AB Sciex, Foster City, Calif.). The half-maximal effective concentration (EC50) of TVB-2640 was determined by following the peak area ratios of newly synthesized palmitate to heptadecanoic acid. All samples were run in duplicate. For each sample, the FASN activity remaining was determined by dividing the individual test article peak area ratio by the average vehicle peak area ratio. The resulting percent inhibition was fit using a 3-parameter model in GraphPad Prism 5 (GraphPad Software, Inc., La Jolla, Calif.) software where the inhibitor concentration was plotted as log 10 concentration verses percent activity. When the inhibition was less than 50% at the highest concentration tested, the EC50 value was reported as greater than the highest concentration tested.

TABLE 2

| Cpd | Hu FASN IC50 (μM) | PMT IC50 (μM) |
|---|---|---|
| 1 | 0.039 | 0.027 |
| 2 | 0.023 | 0.023 |
| 3 | 0.015 | 0.024 |
| 4 | 0.02 | 0.026 |
| 5 | 0.019 | 0.034 |
| 6 | 0.016 | 0.018 |
| 7 | 0.022 | 0.006 |
| 8 | 0.035 | 0.012 |
| 9 |  | 0.056 |
| 10 |  | 0.027 |
| 11 |  | 0.047 |

The data in TABLE 2 represent an average over time of each assays for each compound. For certain compounds, multiple assays have been conducted over the life of the project. Thus, the data reported in TABLE 2 include the data reported in any priority documents, as well as data from assays run in the intervening period.

While preferred aspects of the present disclosure have been shown and described herein, it will be obvious to those skilled in the art that such aspects are provided by way of example only. Numerous variations, changes, and substitutions will now occur to those skilled in the art without departing from the present disclosure. It should be understood that various alternatives to the aspects of the present disclosure described herein can be employed in practicing the present disclosure. It is intended that the following claims define the scope of the present disclosure and that methods and structures within the scope of these claims and their equivalents be covered thereby.

All publications and patent applications cited in this specification are herein incorporated by reference as if each individual publication or patent application were specifically and individually indicated to be incorporated by reference.

What is claimed is:

1. A compound of Formula I:

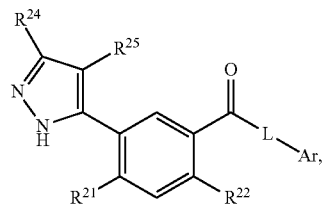

I or a pharmaceutically acceptable salt thereof, wherein:

L-Ar is

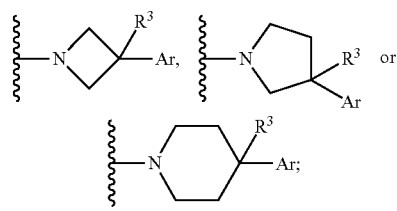

Ar is

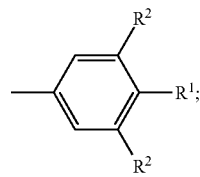

$R^1$ is H, —CN, halogen, $C_1$-$C_4$ alkyl, —O—($C_3$-$C_5$ cycloalkyl), —O-(4- to 6-membered heterocycle) or —O—($C_1$-$C_4$ alkyl), wherein when $R^1$ is not H, —CN or halogen, $R^1$ is optionally substituted with one or more halogen;

each $R^2$ is independently hydrogen, halogen or $C_1$-$C_4$ alkyl;

$R^3$ is H or F;

$R^{21}$ is H, halogen, $C_1$-$C_4$ alkyl, $C_3$-$C_5$ cycloalkyl or 4- to 6-membered heterocycle;

$R^{22}$ is H, halogen or $C_1$-$C_2$ alkyl;

$R^{24}$ is —O—($C_1$-$C_4$ alkyl), —O—($C_1$-$C_4$ alkyl)-O—($C_1$-$C_4$ alkyl), —O—($C_3$-$C_5$ cycloalkyl), or —O-(4- to 6-membered heterocycle), wherein $R^{24}$ is optionally substituted with one or more hydroxyl or halogen; and $R^{25}$ is H, halogen, $C_1$-$C_4$ alkyl or $C_3$-$C_5$ cycloalkyl, wherein $R^{25}$ is optionally substituted with one or more halogen;

wherein the compound is not:

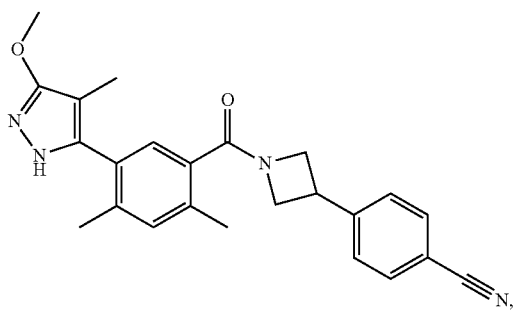

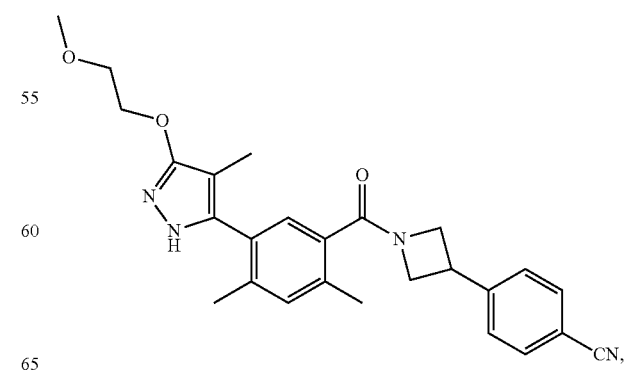

-continued

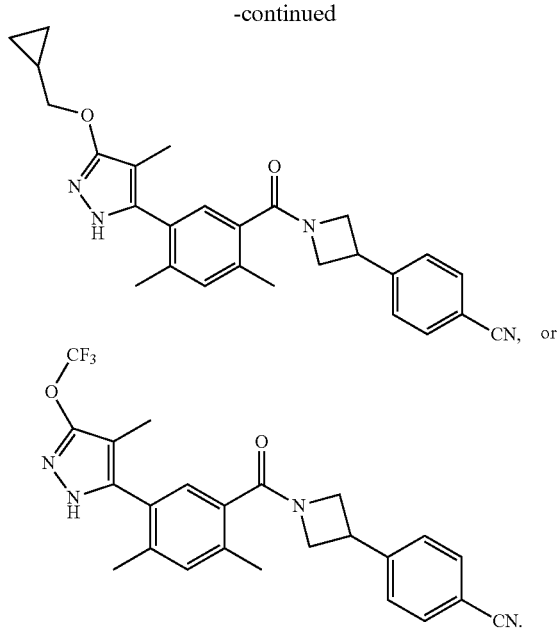

CN, or

2. The compound of claim 1, wherein L-Ar is

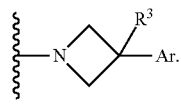

3. The compound of claim 1, wherein L-Ar is

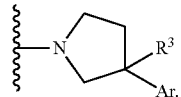

4. The compound of claim 1, wherein L-Ar is

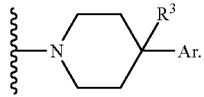

5. The compound of claim 1, wherein $R^3$ is H.
6. The compound of claim 1, wherein $R^1$ is —CN or —O—($C_1$-$C_4$ alkyl), wherein when $R^1$ is not —CN, $R^1$ is optionally substituted with one or more halogen; or $R^1$ is —CN; or $R^1$ is —O—($C_1$-$C_4$ alkyl) optionally substituted with one or more halogen.
7. The compound of claim 1, wherein each $R^2$ is hydrogen.
8. The compound of claim 1, wherein $R^{21}$ is $C_1$-$C_4$ alkyl.
9. The compound claim 1, wherein $R^{22}$ is H or $C_1$-$C_2$ alkyl.
10. The compound of claim 1, wherein $R^{24}$ is —O—($C_1$-$C_4$ alkyl) optionally substituted with one or more hydroxyl or halogen; or $R^{24}$ is —O—($C_1$-$C_4$ alkyl) optionally substituted with one or more hydroxyl.
11. The compound of claim 1, wherein $R^{25}$ is —$CH_3$.

12. The compound of claim 1, having one of the following structures:

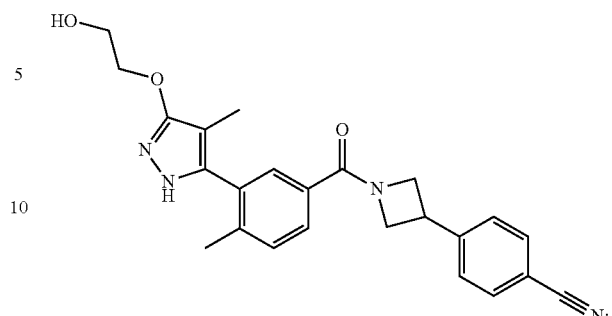

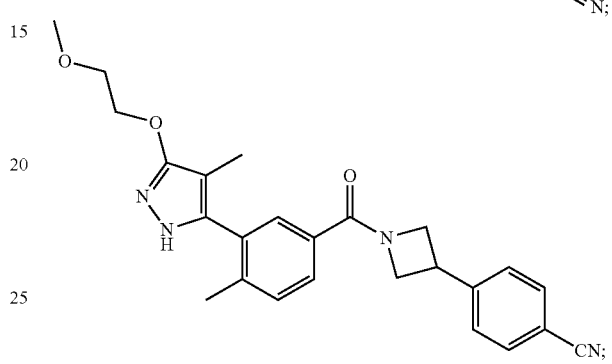

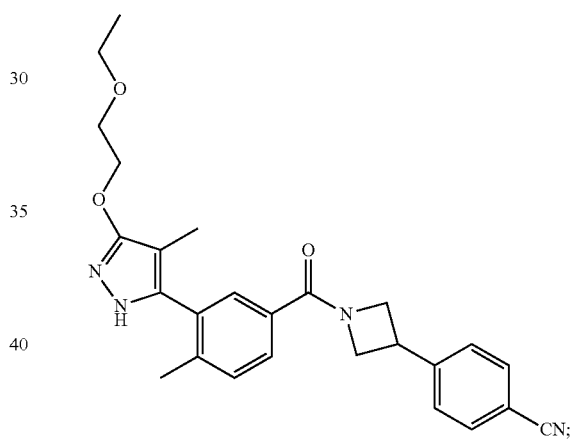

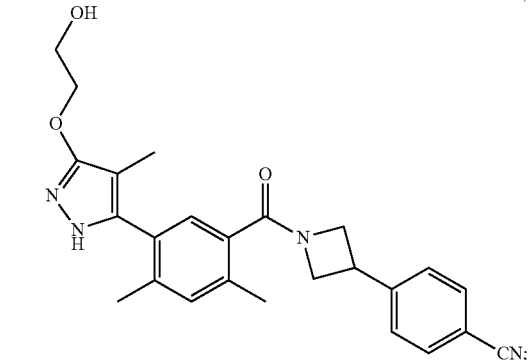

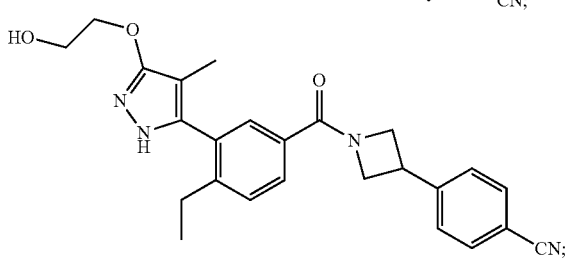

-continued
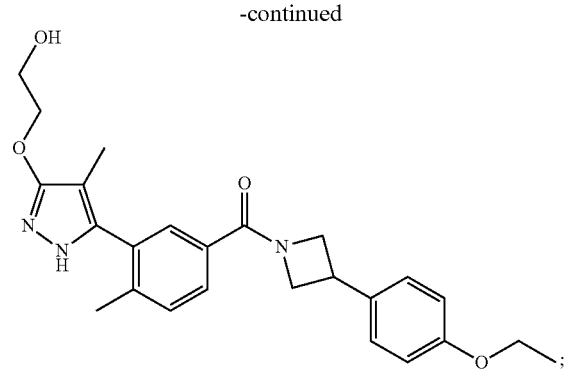
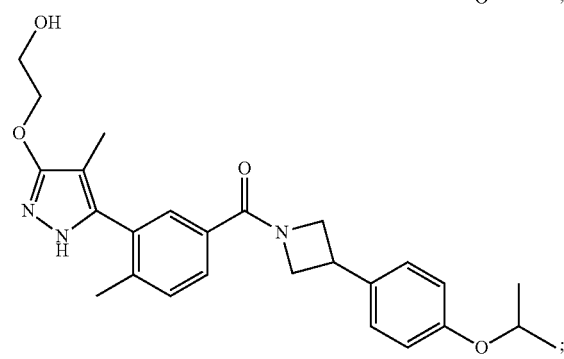
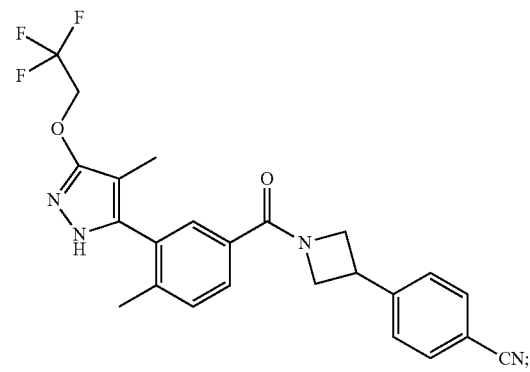
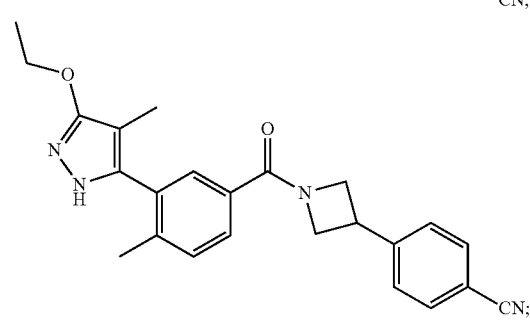
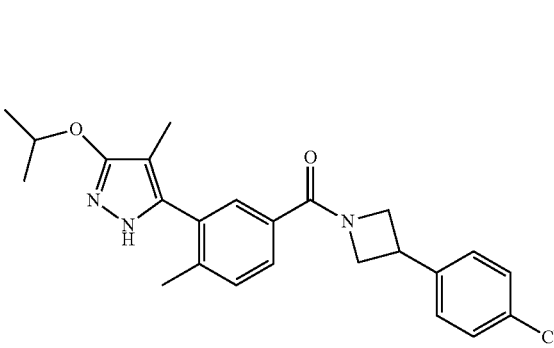
-continued
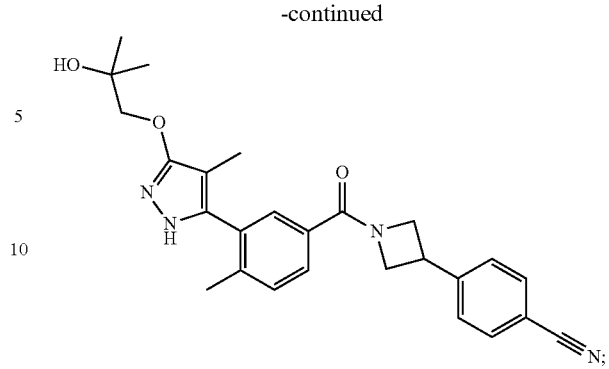
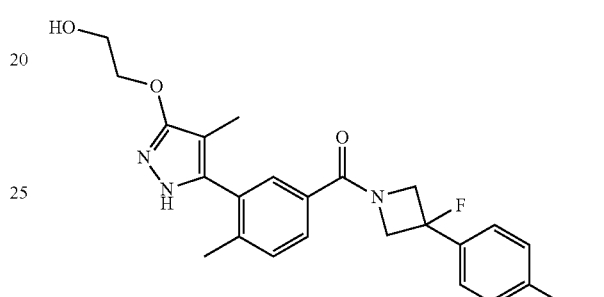
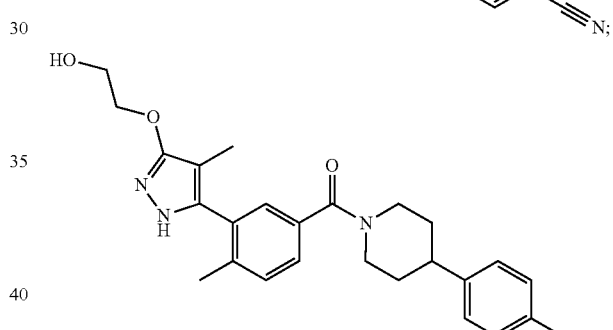
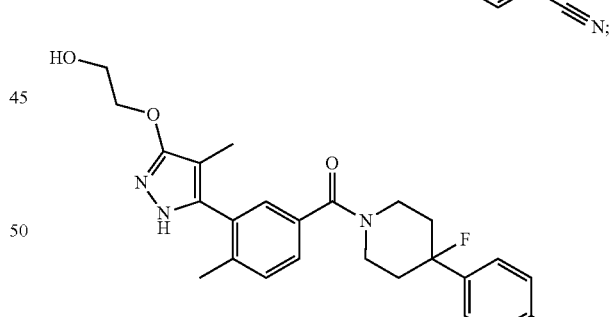
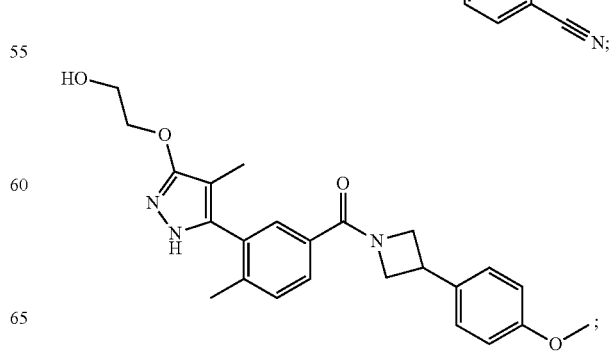

-continued

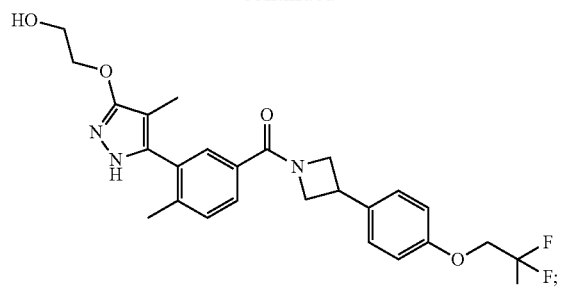

13. The compound of claim 1, wherein the compound is:

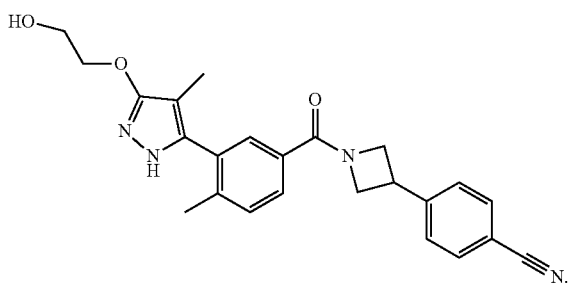 [SMILES: Cc1ccc(C(=O)N2CC(c3ccc(C#N)cc3)C2)cc1-c1[nH]nc(OCCO)c1C]

14. The compound of claim 1, wherein the compound is:

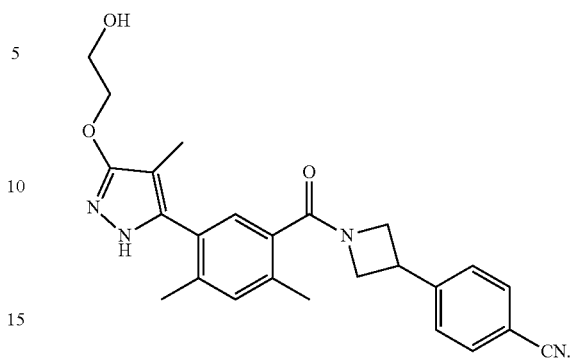

15. A pharmaceutical composition comprising a compound of claim 1, or a pharmaceutically acceptable salt thereof, and a pharmaceutically acceptable carrier, excipient, or diluent.

16. A method of treating a condition characterized by disregulation of a fatty acid synthase pathway in a subject by administering to the subject a therapeutically effective amount of a compound of claim 1, or a pharmaceutically acceptable salt thereof, wherein the condition characterized by disregulation of a fatty acid synthase pathway is a cancer.

17. The method of claim 16, wherein the cancer is selected from the group consisting of breast cancer; mantle cell lymphoma; renal cell carcinoma; acute myelogenous leukemia (AML); chronic myelogenous leukemia (CML); diffuse large B cell lymphoma (DLBCL); sarcoma; rhabdomyosarcoma; ovarian cancer; endometrial tumors; non small cell lung carcinoma (NSCLC); small cell, squamous, large cell and adenocarcinoma; lung cancer; colon cancer; colorectal tumors; KRAS-mutated colorectal tumors; gastric carcinomas; hepatocellular tumors; liver tumors; primary melanomas; pancreatic cancer; prostate carcinoma; thyroid carcinoma; follicular thyroid carcinoma; anaplastic large cell lymphoma (ALCL); hamaratomas, angiomyelolipomas, TSC-associated and sporadic lymphangioleiomyomatosis: Cowden's disease (multiple hamaratoma syndrome); sclerosing hemangioma; Peutz-Jeghers syndrome (PJS); head and neck cancer; neurofibromatosis; macular degeneration; macular edema; myeloid leukemia; systemic lupus; and autoimmune lymphoproliferative syndrome (ALPS).

18. The method of claim 17, further comprising administering a second therapeutic agent, wherein the second therapeutic agent is a cancer therapeutic agent selected from paclitaxel, doxorubicin, vincristine, actinomycin D, altretamine, asparaginase, bleomycin, busulphan, cabazitaxel, capecitabine, carboplatin, carmustine, chlorambucil, cisplatin, cyclophosphamide, cytarabine, dacarbazine, daunorubicin, docetaxel, epirubicin, etoposide, fludarabine, fluorouracil, gemcitabine, hydroxyurea, idarubicin, ifosfamide, irinotecan, lomustine, melphalan, mercaptopurine, methotrexate, mitomycin, mitozantrone, oxaliplatin, procarbazine, steroids, streptozocin, taxotere, tamozolomide, thioguanine, thiotepa, tomudex, topotecan, treosulfan, uracil-tegufur, vinblastine, vindesine, nivolumab, pembrolizumab, MPDL3280A, MEDI4736, olaparib, erlotinib, necitumumab, traztuzumab, pertuzamab, lapatinib, crizotinib, cabozantinib, onartuamab, ramucirumab, bevacizumab, enzalutamide, abiraterone, tamoxifen, cobimetinib, vemurafenib, everolimus, lapatinib, trastuzumab, Kadyzla, sirolimus, avastin, nexavar, sutent, exemtesane, femora, enzalutamide, bicalutamide, Tafinlar, and Zelboraf.

* * * * *